United States Patent
Spiegelman et al.

(10) Patent No.: US 8,097,454 B2
(45) Date of Patent: Jan. 17, 2012

(54) MODEL SYSTEM FOR IDENTIFYING ANTI-CANCER AGENTS

(75) Inventors: Vladimir S. Spiegelman, Fitchburg, WI (US); Neehar Bhatia, Madison, WI (US)

(73) Assignee: Wisconsin Alumni Research Foundation, Madison, WI (US)

(*) Notice: Subject to any disclaimer, the term of this patent is extended or adjusted under 35 U.S.C. 154(b) by 697 days.

(21) Appl. No.: 11/739,182

(22) Filed: Apr. 24, 2007

(65) Prior Publication Data

US 2008/0268438 A1 Oct. 30, 2008

(51) Int. Cl.
*C12N 5/00* (2006.01)
*C12N 15/00* (2006.01)
*C12P 21/06* (2006.01)
*C07H 21/04* (2006.01)

(52) U.S. Cl. .............. 435/325; 435/69.1; 435/320.1; 536/23.5; 536/24.1

(58) Field of Classification Search .............. None
See application file for complete search history.

(56) References Cited

U.S. PATENT DOCUMENTS

2003/0049246 A1* 3/2003 Altaba .............. 424/94.61

OTHER PUBLICATIONS

Bhatia et al in "Gli2 Is Targeted for Ubiquitination and Degradation by β-TrCP Ubiquitin Ligase" (JBC, vol. 281, No. 28, pp. 19320-19326, published May 1, 2006).*

* cited by examiner

*Primary Examiner* — Nancy Vogel
*Assistant Examiner* — Catherine Hibbert
(74) *Attorney, Agent, or Firm* — Kening Li; Pinsent Masons LLP

(57) ABSTRACT

A model system for screening and identification of compounds that interfere with Gli2 dependent tumorigenesis and provide potential use as anticancer agents is provided. In particular, the invention includes a Gli2 protein having an S662A point mutation that interferes with binding by the ubiquitin-ligase β-TrCP. The mutation inhibits Gli2 degradation by the ubiquitin pathway. Gli2 stability and half-life are increased in the host cell resulting in an increase in Gli2-dependent transcription and concomitant neoplasia and tumorigenesis. Expression of the Gli2 mutant allows for the high throughput screening of compounds that interfere with the tumorigenesis thereby identifying anticancer agents.

5 Claims, 5 Drawing Sheets

MODEL SYSTEM FOR IDENTIFYING ANTI-CANCER AGENTS

STATEMENT AS TO RIGHTS TO INVENTIONS MADE UNDER FEDERALLY SPONSORED RESEARCH AND DEVELOPMENT

This work was supported in part with United States government support awarded by the following agencies ARMY/MRMC W81XWH-05-1-0415. The United States has certain rights in this invention.

FIELD OF THE INVENTION

This invention provides a method of initiating neoplastic cascades and identifying agents that interfere therewith. In particular, the method includes an isolated polypeptide and vector which results in the constitutive expression of the hedgehog cascade.

BACKGROUND OF THE INVENTION

Hedgehog (Hh) signaling plays a prominent role in embryogenesis, and its deregulation is implicated in tumorigenesis. Cellular responses to the Hedgehog (Hh) signal are controlled by two transmembrane proteins: the tumor suppressor Patched (PTCH) and the proto-oncogene Smoothened (SMO). In the absence of secreted Hh proteins, PTCH actively silences intracellular signaling by inactivating SMO. During physiologic signaling, Hh proteins bind and inactivate PTCH, which alleviates PTCH-mediated suppression of SMO. SMO activation triggers a series of intracellular events, culminating in expression of Hh target genes through the action of the Gli family of transcription factors. Gli1, Gli2 and Gli3, and their *Drosophila* homolog, Cubitus interruptus (Ci), are zinc finger transcription factors that are downstream effectors of Hh signaling. In the absence of Hh signaling, Ci is truncated at the carboxyl terminal domain to form a truncated repressor protein, whereas Hh activation leads to accumulation of transcriptionally active, full length Ci. The situation with mammalian Gli proteins is more complex. Gli3 functions primarily as a C-terminally truncated repressor, but full-length Gli3 protein accumulates in cells responding to Hh. Gli1, on the other hand, appears to modulate gene expression by acting primarily as a transcriptional activator, but Gli1 mutant mice are phenotypically normal, arguing against an essential function for this protein during development or postnatal life. Gli2 appears to be the major nuclear effector of Hh signaling in vivo and functions primarily as a transcriptional activator. However, little is known about the molecular mechanisms regulating Gli2 expression at the protein level.

The Hh signaling pathway is deregulated in many human malignancies, including skin cancer, such as, basal cell carcinoma (BCC), medulloblastoma, glioblastoma, rhabdomyosarcoma, lung, prostate, breast, and some gastrointestinal cancers. Recent studies have stressed the importance of Hh signaling in human prostate cancer. Elevated Hh signaling pathway activity may distinguish metastatic from localized prostate cancer, and pathway manipulation can modulate invasiveness and metastasis. In contrast to BCCs and mebulloblastomas, which are associated with inactivating mutations in PTCH or gain-of-function mutations in SMO, aberrant Hh signaling in prostate cancers appears to be the result of constitutive overexpression of Sonic hedgehog (SHH). Hence, the growth of many of the prostate cancer cells is inhibited by Hh-neutralizing antibody. Furthermore, cyclopamine, a steroidal alkaloid that interacts with SMOH directly thus inhibiting Hh signaling, was shown to induce apoptosis and inhibit proliferation of prostate cancer cells in vivo as well as in vitro.

The ubiquitin-proteasome pathway is essential for degradation of proteins regulating growth and cell cycle progression. Ubiquitin-activating enzyme (E1), ubiquitin-conjugating enzyme (E2) and ubiquitin-ligase (E3) sequentially tag proteins for ubiquitination and proteasomal degradation. SCF E3 ubiquitin ligases are composed of Skp1, Cul1, Roc1 and F box proteins, where F box proteins are substrate recognizing subunits. Beta-transducin repeat-containing F box proteins (β-TrCP) recognize substrates phosphorylated within the $DSG(X)_{2+n}S$ destruction motifs. $SCF^{\beta-TrCP}$ E3 ligases ubiquitinate specifically phosphorylated substrates and play a pivotal role in the regulation of cell division and various signal transduction pathways, which, in turn, are essential for many aspects of tumorigenesis. Genetic data have suggested that *Drosophila* slimb protein (orthologue of mammalian β-TrCP) is involved in proteolytic processing of Ci155 to Ci75. However, there is no biochemical evidence that Slimb/β-TrCP proteins are involved in ubiquitination and degradation of Ci/Gli transcription factors.

Stabilization of the transcription factor Gli2 has been suggested as a key event in the transduction of Hh signals. The potential role of Gli2 in the development of BCC has been well documented. Gli2 is over-expressed in the majority of human BCCs, and skin-targeted over-expression of Gli2 in transgenic mice leads to the development of multiple BCCs. There is growing evidence that the transcriptional regulation of some Hh target genes, including Gli1, E2F1, Bcl2, etc., are Gli2 dependent. The promoter of one such gene, Bcl2, is regulated preferentially by Gli2.

As disclosed herein, the inventors have found that $SCF^{\beta-TrCP}$ E3 ubiquitin ligase is responsible for Gli2 degradation. β-TrCP2 binds wild type Gli2 and promotes its ubiquitination, which can be altered by a single amino acid substitution in the DSGX binding site of Gli2 with β-TrCP2. As disclosed here, mutating residues within the DSGX binding motif, inhibits binding of β-TrCP2 to Gli2, increasing Gli2 half-life and promoting Gli2 dependent transcription. The inventors further show that Gli2 is over-expressed in prostate cancer cell lines and primary tumors. Thus, expression of Gli2 with altered binding to β-TrCP2 provides a model for investigating diseases identified with Gli2 overexpression and for identifying agents that interfere with Gli2 dependent transcription and/or diseases resulting therefrom.

SUMMARY OF THE INVENTION

The invention provides compositions and methods to direct cells to a neoplastic state. In particular, the invention includes a Gli2 protein having a point mutation that interferes with binding by the ubiquitin-ligase β-TrCP, thus, inhibiting Gli2 degradation by the ubiquitin pathway. Gli2 stability and half-life are increased in the mutant resulting in an increase in Gli2-dependent transcription and concomitant neoplasia and tumorigenesis. The invention provides a model for the screening and identification of compounds that interfere with Gli2-dependent tumorigenesis to provide use as anticancer agents.

A model system for screening and identification of compounds that interfere with Gli2 dependent tumorigenesis and provide potential use as anticancer agents is provided. In particular, the invention includes a Gli2 protein having an S662A point mutation that interferes with binding by the ubiquitin-ligase β-TrCP. The mutation inhibits Gli2 degradation by the ubiquitin pathway. Gli2 stability and half-life are increased in the host cell resulting in an increase in Gli2- dependent transcription and concomitant neoplasia and tumorigenesis. Expression of the Gli2 mutant allows for the high throughput screening of compounds that interfere with the tumorigenesis thereby identifying anticancer agents.

Therefore, in one exemplary embodiment, the invention includes an isolated polypeptide having the sequence set forth in SEQ ID NO:6, comprising the Gli2$^{S662A}$ mutant. In some embodiments, the invention includes a host cell, the genome of which is augmented with the nucleic acid molecule encoding the amino acid sequence set forth in SEQ ID NO:6. In still other exemplary embodiments the invention further includes an isolated polynucleotide having the sequence set forth in SEQ ID NO: 5 or conservative variations thereof wherein the polynucleotide codes for the expression of an amino acid sequence as set forth in SEQ ID NO:6.

In another exemplary embodiment, the invention includes an isolated polypeptide coding for the Gli2 transcription factor set forth in SEQ ID NO:6, wherein the β-TrCP2 binding motif DSGV/M is mutated to $Xaa_1Xaa_2Xaa_3Xaa_4$, wherein $Xaa_1$ represents any amino acid except aspartic acid, $Xaa_2$ represents any amino acid except for serine, $Xaa_3$ represents any amino acid except for glycine and $Xaa_4$ represents any amino acid except valine or methionine such that Gli2 no longer binds β-TrCP2. Further, in some aspects according to the invention, the invention further includes a host cell comprising a genome which is augmented with a nucleic acid molecule encoding the polypeptide set forth in SEQ ID NO:6 wherein the DSGV/M binding motif is disrupted. In still other aspects, the invention further includes an isolated polynucleotide coding for a Gli2 polypeptide having a disrupted βTrCP2 binding motif.

In still another exemplary embodiment the invention includes a bioassay for evaluating the efficacy of anticancer agents. In this embodiment, the invention comprises:
  (a) culturing cells which contain non-endogenous DNA which expresses a Gli2$^{S662A}$ protein having the sequence set forth in SEQ ID NO:6;
  (b) expressing the non-endogenous DNA in the cultured cells;
  (c) identifying the transformation to a neoplastic state of the cells;
  (d) assaying for compounds that inhibit or ameliorate the transformation to a neoplastic state; thereby evaluating the efficacy of anticancer agents.

In some versions, this embodiment further includes a reporter plasmid wherein the reporter plasmid includes one or more copies of 3' Gli binding sites and where binding of the Gli2 the binding site results in expression of a reporter gene. In various exemplary embodiments, the bioassay further includes a reporter gene. In various exemplary embodiments, the reporter gene may comprise luciferase, β galactosidase, green fluorescent protein or combinations thereof.

In still other exemplary embodiments, the invention includes a bioassay for identifying inhibitors of the hedgehog signaling pathway comprising:
  (a) culturing cells which contain non-endogenous DNA which expresses a Gli2$^{S662A}$ protein having the sequence set forth in SEQ ID NO:5;
  (b) expressing the non-endogenous DNA in the cultured cells;
  (c) identifying an increase in the hedgehog signaling pathway;
  (d) contacting the cells with a compound that inhibits the increase in the hedgehog cascade;
thereby identifying inhibitors of the hedgehog signaling pathway.

In still other preferred embodiments, the invention includes an expression vector encoding the isolated polypeptide of SEQ ID NO. 2, operatively linked to a promoter. In some embodiments, the promoter is an inducible promoter. However, in still other embodiments, the promoter is a constitutive promoter.

Other objects, features and advantages of the present invention will become apparent after review of the specification, claims and drawings.

BRIEF DESCRIPTION OF THE DRAWINGS

FIG. 1A is a map of the Flag-mGli2 pc, plasmid; FIG. 1B is a schematic illustrating the cloning strategy for introducing the S662A point mutation into the Gli2 cDNA. Primer3 (SEQ ID NO: 3) and primer4 (SEQ ID NO: 4) are shown along with the wild type sequence (SEQ ID NO: 5) to which the two primers anneal.

FIGS. 2A-2E, are data illustrating that β-TrCP2 interacts with Gli2, and promotes its ubiquitination in vivo. FIG. 2A is a homology chart showing that the β-TrCP recognition motif in Gli2 is conserved across different species (SEQ ID NOs: 7-13). FIG. 2B are western blots illustrating the interaction of wild-type (WT) Gli2 or the mutant Gli2$^{S662A}$ protein. A representative of three independent experiments is shown. IP=immuno precipitation, IB=immuno blot. FIG. 2C is an immunoblot illustrating the interaction between endogenous proteins as shown. WCE=whole cell extract. FIG. 2D, top panel is a radiogram showing the binding of in vitro-translated and .sup.35S-labeled .beta.-TrCP2 to Flag-Gli2 proteins expressed in 293T cells and immunopurified with Flag antibody before or after treatment with protein phosphatase . lamda. FIG. 2E shows the in vivo ubiquitination of Flag-Gli2 (wild type or S662A mutant) in 293T cells co-transfected with HA-tagged ubiquitin and .beta.-TrCP2 constructs as indicated. Immunoprecipitation reactions with Flag antibodies were analyzed by means of immunoblotting with HA antibody. Ubiquitinated Flag-Gli2 species ("Gli2.about.Ub") are indicated. A representative of two independent experiments is shown.

FIG. 3A, top panel autoradiograph of Flag-Gli2$^{wt}$ in shRNA transfected 293T cells, metabolically labeled with $^{35}$S-methionine/$^{35}$S-cysteine, cells were harvested at time points indicated. Lower panel is a graph depicting percent of remaining Gli2 (compared to time point "0"). Insert shows the levels of β-TrCP1 and β-TrCP2 expression in 293T cells transfected with the indicated shRNA analyzed by immunoblotting. FIG. 3B, top panel is an autoradiograph of pulse chase analysis of Flag-Gli2$^{wt}$ protein expressed in 293T cells with or without dominant negative HA-tagged β-TrCP2$^{ΔN}$ mutant and analyzed as in FIG. 3A. Lower panel is a graph depicting the percent of remaining Gli2 (compared to time point "0"). Insert shows the levels of HA-β-TrCP2$^{ΔN}$ expression in 293T cells transfected analyzed by immunoblotting with HA antibody. FIG. 3C, pulse chase analysis of endogenous Gli2 protein in 293T cells with or without dominant negative HA-tagged β-TrCP2$^{ΔN}$ mutant. 293T cells were metabolically labeled with $^{35}$S-methionine/$^{35}$S-cysteine. Cells were harvested at different time points of chase with unlabeled methionine and cysteine. Gli2 was immunoprecipitated with Gli2 antibody (Santa Cruz Biotechnology) and analyzed using autoradiography. A representative of two independent experiments is shown. Insert shows the levels of HA-β-TrCP2$^{ΔN}$ expression in 293T cells transfected analyzed by immunoblotting with HA antibody. FIG. 3D is an immunoblot with GLI2 antibody showing the effect of the expression of the endogenous expression of GLI2 protein in 293T cells transfected with the indicated shRNA constructs. FIG. 2E top panel is an autoradiograph of pulse chase analysis of Flag-Gli2$^{wt}$ protein expressed in 293T cells treated with LiCl and analyzed as in FIG. 3A, bottom panel is a graph depicting the percent of remaining Gli2 (compared to time point "0"). Cells were serum starved for 12 hr and then treated with 40 mM LiCl 1 hr prior to the chase. A representative of two independent experiments is shown.

FIGS. 4A-4C are data showing that Gli2$^{S662A}$ is expressed in higher levels and is more potent in the activation of Gli-dependent transcription than Gli2$^{wt}$. FIG. 4A top panel autoradiograph of Gli2$^{wt}$ and Gli$^{S662A}$ transfected 293T cells, metabolically labeled with $^{35}$S-methionine/$^{35}$S-cysteine, and their degradation; cells were harvested at the time pointes indicated. Lower panel is a graph depicting percent of remaining Gli2 and Gli$^{S662A}$ (compared to time point "0"). A representative of two experiments is shown. FIG. 4B similar to 3A, top panel is an autoradiograph of a pulse chase analysis of Flag-Gli2$^{S662A}$ protein expressed in 293T cells with or without dominant negative β-TrCP2$^{\Delta N}$ mutant and analyzed as in FIG. 3A. A representative of two independent experiments is shown. Lower panel is a graph depicting percent of remaining Gli$^{S662A}$ for each construct (compared to time point "0"). Insert shows the levels of HA-β-TrCP2$^{\Delta N}$ expression in 293T cells transfected, analyzed by immunoblotting with HA antibody. FIG. 4C graphs representing results of luciferase assay for HeLa cells transfected with Gli-luciferase (8×3'Gli BS-LucII), pGL3-Bcl2promo luciferase, or K17 luciferase, and respective Gli2 expression plasmids as indicated. Luciferase activity was estimated using Luciferase Reporter Assay Reagent (Promega, Madison, Wis.). β-galactosidase was used for normalization and estimated using β-gal assay reagent (Pierce Biotechnology). *–p<0.01 compared to cells transfected with empty vector (pcDNA3.1); **–p<0.01 compared to cells transfected with Gli2wt, in Student's t-test. Insert shows the levels of Flag-Gli2 expression in HeLa cells transfected with Flag-Gli2$^{wt}$ or Flag-Gli2$^{S662A}$ analyzed by immunoblotting with Gli2 G-20 antibody (protein loading was normalized by β-galactosidase activity).

FIG. 5B histogram showing expression of GLI2 mRNA in the prostate cancer cell lines shown in FIG. 5A as assessed by Real Time RT-PCR. GAPDH was used as an internal control. A representative of three independent experiments is shown. FIG. 5C shows histochemical preparations of prostate hyperplasia (left panel) and adenocarcinoma (right panel) at ×400 magnification. Gli2 antibody was used for immunostaining.

DETAILED DESCRIPTION OF THE EXEMPLARY EMBODIMENTS

Figures 1A, 1B:
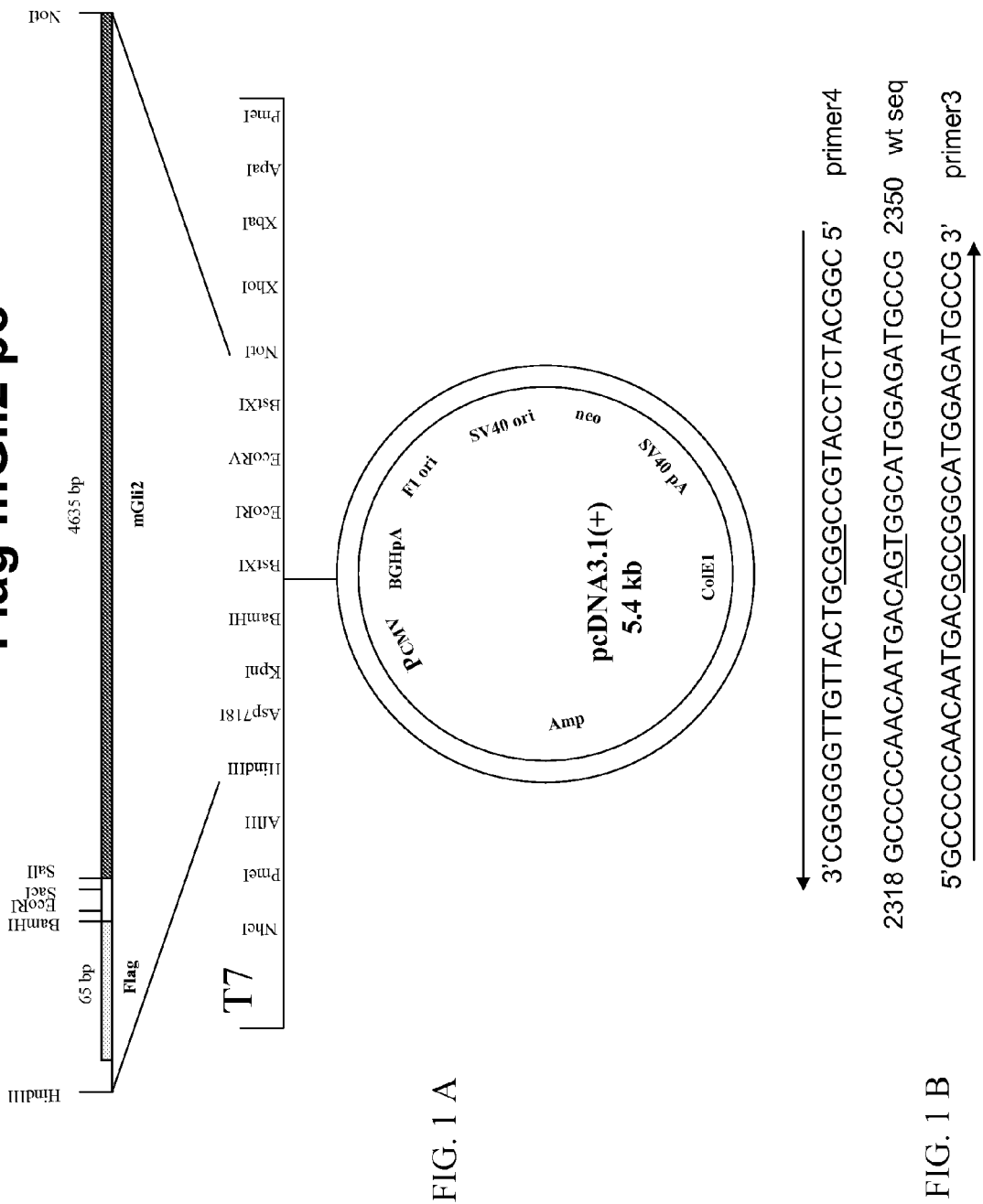
FIGS. 1A and 1B, are maps of the Flag-MGli2 expression vector.

Before the present polypeptides, nucleic acids, and methods are described, it is understood that this invention is not limited to the particular methodology, protocols, cell lines, vectors, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the polypeptides, polynucleotides, strains, vectors, and methodologies which are reported in the publications which might be used in connection with the invention. Nothing herein is to be construed as an admission that the invention is not entitled to antedate such disclosure by virtue of prior invention.

The practice of the present invention will employ, unless otherwise indicated, conventional techniques of molecular biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Cell Culture and Somatic Cell Genetics of Plants, Vol. 1 (I. K. Vasil, ed. 1984); R. V. Stanier, J. L. Ingraham, M. L. Wheelis, and P. R. Painter, The Microbial World, (1986) 5th Ed. Prentice-Hall.

Definitions

The Hedgehog (Hh) signaling pathway plays a crucial role in embryogenesis and has been linked to the development of several human malignancies. The transcription factor Gli2 plays a key role in the transduction of Hh signals by modulating transcription of some Hh target genes, yet, the mechanisms that control Gli2 protein expression are largely unknown. As disclosed herein, β-TrCP E3 ubiquitin ligase is required for Gli2 degradation. β-TrCP2 directly binds wild type Gli2 and promotes its ubiquitination. Single amino acid substitution in Gli2 putative binding site inhibits its interaction with β-TrCP2, its ubiquitination, and stabilizes the Gli2 protein. Stable Gli2 mutant is expressed in higher levels and is more potent in the activation of Gli-dependent transcription as compared with wild type Gli2. The inventors also found that GLI2 protein is highly expressed in prostate cancer cell lines and primary tumors, whereas the level of GLI2 mRNA is not appreciable different in normal and neoplastic prostate. These data identify β-TrCP2 as a pivotal regulator of Gli2 expression, and point to an important role for post-translational modulation of GLI2 protein levels in Hh pathway-associated human prostate cancer.

The term "biologically active" or "physiologically active", as used herein, refers to a protein, polypeptide, amino acid sequence, or nucleotide sequence encoding a product having structural, regulatory, or biochemical functions of a naturally occurring molecule. For example, a biologically active fragment of HdaA will have the histone deacetylase capabilities of a naturally occurring HdaA molecule disclosed herein.

Figure 2:
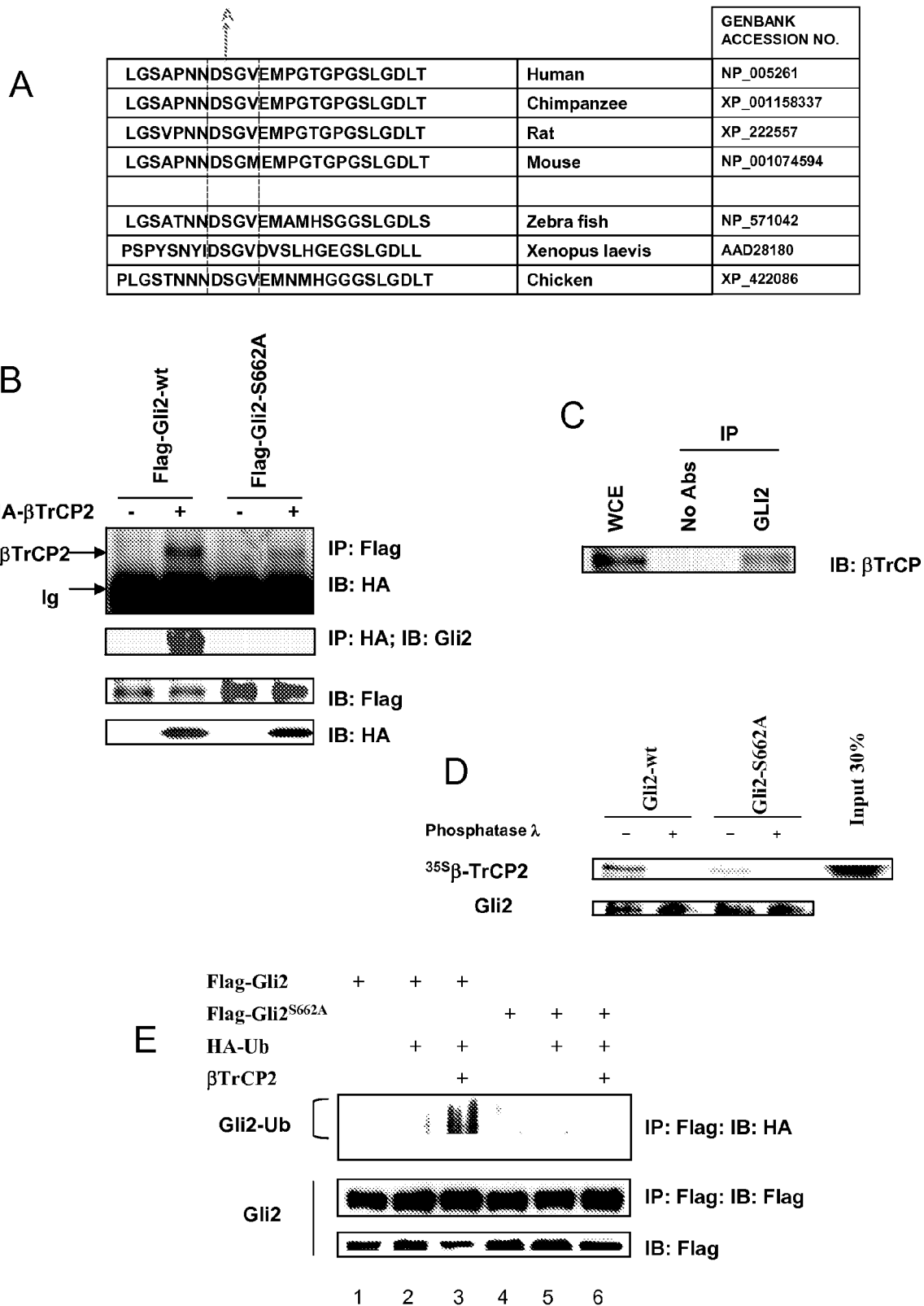

"Gli2", as used herein, refers to the amino acid sequences of the Gli2 protein obtained from Mammals and having the amino acid sequence given in GENBANK accession No. NP_005261 (See, FIG. 2A). In addition, Gli2 shall also refer to the amino acid sequences of Gli2 or other transcription factors obtained from any species (i.e., orthologs), from any source whether natural, synthetic, semi-synthetic, or recombinant. The term encompasses proteins encoded by nucleotide sequences representing allelic variants as well as those containing single nucleotide polymorphisms (SNPs).

"gli2", as used herein, refers to the nucleotide sequences of the gli2 gene obtained from Mus musculus (GenBank accession no. NP_001074594). In addition, gli2 shall also refer to the nucleotide sequences of the gli2 gene or other transcription factors obtained from any species, particularly mammals, from any source whether natural, synthetic, semi-synthetic, or recombinant. The term encompasses allelic variants and single nucleotide polymorphisms (SNPs).

"Single nucleotide polymorphism" or "SNPs" are defined by their characteristic attributes. A central attribute of such a polymorphism is that it contains a polymorphic site, "X," most preferably occupied by a single nucleotide, which is the site of the polymorphism's variation (Goelet and Knapp U.S. patent application Ser. No. 08/145,145). Methods of identifying SNPs are well known to those of skill in the art (see, e.g., U.S. Pat. No. 5,952,174).

A "composition comprising a given polynucleotide sequence", as used herein, refers broadly to any composition containing the given polynucleotide sequence. Compositions comprising polynucleotide sequences encoding gli2 or fragments thereof, may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., SDS) and other components (e.g., Denhardt's solution, dry milk, salmon sperm DNA, etc.).

The term "correlates with expression of a polynucleotide", as used herein, indicates that the detection of the presence of ribonucleic acid is indicative of the presence of mRNA encoding, for example, Gli2 in a sample and thereby correlates with expression of the transcript from the polynucleotide encoding the protein.

A "deletion", as used herein, refers to a change in the amino acid or nucleotide sequence and results in the absence of one or more amino acid residues or nucleotides.

The term "homology", as used herein, refers to sequence similarity between two peptides or between two nucleic acid molecules. Homology may be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. A partially complementary sequence that at least partially inhibits an identical sequence from hybridizing to a target nucleic acid is referred to using the functional term "substantially homologous. The inhibition of hybridization of the completely complementary sequence to the target sequence may be examined using a hybridization assay (Southern or northern blot, solution hybridization and the like) under conditions of low stringency. A substantially homologous sequence or hybridization probe will compete for and inhibit the binding of a completely homologous sequence to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementary (e.g., less than about 30% identity). In the absence of non-specific binding, the probe will not hybridize to the second non-complementary target sequence.

In the art, "identity" means the degree of sequence relatedness between polypeptide or polynucleotide sequences, as the case may be, as determined by the match between strings of such sequences. "Identity" and "homology" can be readily calculated by known methods, including but not limited to those described in (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48: 1073 (1988). Preferred methods to determine identity are designed to give the largest match between the sequences tested. Methods to determine identity and homology are codified in publicly available computer programs. Preferred computer program methods to determine identity and homology between two sequences include, but are not limited to, the GCG program package (Devereux, J., et al., Nucleic Acids Research 12(1): 387 (1984)), BLASTP, BLASTN, and FASTA (Atschul, S. F. et al., J. Molec. Biol. 215: 403-410 (1990). The BLAST X program is publicly available from NCBI and other sources (BLAST Manual, Altschul, S., et al, NCBI NLM NIH Bethesda, Md. 20894; Altschul, S., et al., J. Mol. Biol. 215: 403-410 (1990). The well known Smith Waterman algorithm may also be used to determine identity.

"Altered" or "modified" nucleic acid sequences encoding, for example, Gli2 as used herein, include those with deletions, insertions, or substitutions of different nucleotides resulting in a polynucleotide that encodes the same or a functionally equivalent protein. Included within this definition are polymorphisms which may or may not be readily detectable using a particular oligonucleotide probe of the polynucleotide encoding the subject protein, and improper or unexpected hybridization to alleles, with a locus other than the normal chromosomal locus for the respective polynucleotide sequence. The encoded protein may also be "altered" and contain deletions, insertions, or substitutions of amino acid residues which produce a silent change and result in a functionally equivalent protein. Deliberate amino acid substitutions may be made on the basis of similarity in polarity, charge, solubility, hydrophobicity, hydrophilicity, and/or the amphipathic nature of the residues as long as the biological or immunological activity of the subject protein is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine, glycine and alanine, asparagine and glutamine, serine and threonine, and phenylalanine and tyrosine.

"Amino acid sequence", as used herein, refers to an oligopeptide, peptide, polypeptide, or protein sequence, and fragment thereof. Where "amino acid sequence" is recited herein to refer to a particular amino acid sequence "amino acid sequence", and like terms, are not meant to limit the amino acid sequence to the complete amino acid sequence referenced but shall be understood to include fragments of the complete amino acid sequence. The term shall further encompass synthetic molecules as well as those occurring naturally. The term "portion" or "fragment", as used herein, with regard to an amino acid sequence, specifically refers to segments of that amino acid sequence which are not naturally occurring as fragments and would not be found in the natural state. The segments may range in size from five amino acid residues to the entire amino acid sequence minus one amino acid.

"Amplification", as used herein, refers to the production of additional copies of a nucleic acid sequence and is generally carried out using polymerase chain reaction (PCR) technologies well known in the art (Dieffenbach, C. W. and G. S. Dveksler (1995) PCR Primer, a Laboratory Manual, Cold Spring Harbor Press, Plainview, N.Y.).

An "insertion", "addition", or "mutation" as used herein, refers to a change in an amino acid or nucleotide sequence resulting in the addition or change of one or more amino acid residues or nucleotides, respectively, as compared to the naturally occurring molecule. Thus, the nomenclature $Gli^{S662A}$ mutant refers to a protein that has a change in from serine to arginine at residue 662 of its amino acid sequence.

"Isolated" or "purified" or "isolated and purified" means altered "by the hand of man" from its natural state, i.e., if it occurs in nature, it has been changed or removed from its original environment, or both. For example, a polynucleotide or a polypeptide naturally present in a living organism is not "isolated," but the same polynucleotide or polypeptide separated from the coexisting materials of its natural state is "isolated", as the term is employed herein. Moreover, a polynucleotide or polypeptide that is introduced into an organism by transformation, genetic manipulation or by any other recombinant method is "isolated" even if it is still present in said organism, which organism may be living or non-living. As so defined, "isolated nucleic acid" or "isolated polynucleotide" includes nucleic acids integrated into a host cell chromosome at a heterologous site, recombinant fusions of a native fragment to a heterologous sequence, recombinant vectors present as episomes or as integrated into a host cell chromosome. As used herein, the term "substantially purified", refers to nucleic or amino acid sequences that are removed from their natural environment, isolated or separated, and are at least 60% free, preferably 75% free, and most preferably 90% free from other components with which they are naturally associated. As used herein, an isolated nucleic acid "encodes" a reference polypeptide when at least a portion of the nucleic acid, or its complement, can be directly translated to provide the amino acid sequence of the reference polypeptide, or when the isolated nucleic acid can be used, alone or as part of an expression vector, to express the reference polypeptide in vitro, in a prokaryotic host cell, or in a eukaryotic host cell.

"Nucleic acid sequence" or "nucleotide sequence" or polynucleotide sequence", as used herein, refers to an oligonucleotide, nucleotide, or polynucleotide, and fragments thereof, and to DNA or RNA of genomic or synthetic origin which may be single- or double-stranded, and represent the sense or antisense strand. Where "nucleic acid sequence" or "nucleotide sequence" or polynucleotide sequence" is recited herein to refer to a particular nucleotide sequence "nucleotide sequence", and like terms, are not meant to limit the nucleotide sequence to the complete nucleotide sequence referenced but shall be understood to include fragments of the complete nucleotide sequence. In this context, the term "fragment" may be used to specifically refer to those nucleic acid sequences which are not naturally occurring as fragments and would not be found in the natural state. Generally, such fragments are equal to or greater than 15 nucleotides in length, and most preferably includes fragments that are at least 60 nucleotides in length. Such fragments find utility as, for example, probes useful in the detection of nucleotide sequences encoding Gli2.

A "substitution", as used herein, refers to the replacement of one or more amino acids or nucleotides by different amino acids or nucleotides, respectively. The term "conservative substitution" is used in reference to proteins or peptides to reflect amino acid substitutions that do not substantially alter the activity (specificity or binding affinity) of the molecule. Typically conservative amino acid substitutions involve substitution one amino acid for another amino acid with similar chemical properties (e.g. charge or hydrophobicity). The following six groups each contain amino acids that are typical conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W).

A "plasmid" is a DNA molecule separate form the chromosomal DNA and capable or autonomous replication. "Expression vectors" are defined herein as nucleic acid sequences that direct the transcription of cloned copies of genes/cDNAs and/or the translation of their mRNAs in an appropriate host. Such vectors can be used to express genes or cDNAs in a variety of hosts such as bacteria, bluegreen algae, plant cells, insect cells and animal cells. Expression vectors include, but are not limited to, cloning vectors, modified cloning vectors, specifically designed plasmids or viruses. Specifically designed vectors allow the shuttling of DNA between hosts, such as bacteria-yeast or bacteria-animal cells. An appropriately constructed expression vector preferably contains: an origin of replication for autonomous replication in a host cell, a selectable marker, optionally one or more restriction enzyme sites, optionally one or more constitutive or inducible promoters. In preferred embodiments, an expression vector is a replicable DNA construct in which a DNA sequence encoding a described protein or a fragment thereof is operably linked to suitable control sequences capable of effecting the expression of the products in a suitable host. Control sequences include a transcriptional promoter, an optional operator sequence to control transcription and sequences which control the termination of transcription and translation, and so forth.

"Transformation" or "transfection", as defined herein, describes a process by which exogenous DNA enters and changes a recipient cell. It may occur under natural or artificial conditions using various methods well known in the art. Transformation and transfection may rely on any known method for the insertion of foreign nucleic acid sequences into a prokaryotic or eukaryotic host cell. The method is selected based on the type of host cell being transformed and may include, but is not limited to, viral infection, electroporation, heat shock, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The term also includes variations on the traditional peptide linkage joining the amino acids making up the polypeptide. Where the terms are recited herein to refer to a polypeptide, peptide or protein of a naturally occurring protein molecule, the terms are not meant to limit the polypeptide, peptide or protein to the complete, native amino acid sequence associated with the recited protein molecule but shall be understood to include fragments of the complete polypeptide. The term "portion" or "fragment", as used herein, with regard to a protein or polypeptide (as in "a fragment of the Gli2 polypeptide") refers to segments of that polypeptide which are not naturally occurring as fragments in nature. The segments may range in size from five amino acid residues to the entire amino acid sequence minus one amino acid. Thus, a polypeptide encompasses the full-length amino acid sequence as well as segments thereof. Fragments of a described protein preferably are biologically active as defined herein.

The terms "nucleic acid" or "oligonucleotide" or "polynucleotide" or grammatical equivalents herein refer to at least two nucleotides covalently linked together. A nucleic acid of the present invention is preferably single-stranded or double stranded and will generally contain phosphodiester bonds, although in some cases, as outlined below, nucleic acid analogs are included that may have alternate backbones, comprising, for example, phosphoramide (Beaucage et al. (1993) *Tetrahedron* 49:1925) and references therein; Letsinger (1970) *J. Org. Chem.* 35:3800; Sprinzl et al. (1977) *Eur. J. Biochem.* 81: 579; Letsinger et al. (1986) *Nucl. Acids Res.* 14: 3487; Sawai et al. (1984) *Chem. Lett.* 805, Letsinger et al. (1988) *J. Am Chem. Soc.* 110: 4470; and Pauwels et al. (1986) *Chemica Scripta* 26: 141 9), phosphorothioate (Mag et al. (1991) *Nucleic Acids Res.* 19:1437; and U.S. Pat. No. 5,644, 048), phosphorodithioate (Briu et al. (1989) *J. Am. Chem. Soc.* 111:2321, O-methylphophoroamidite linkages (see Eckstein, *Oligonucleotides and Analogues: A Practical Approach*, Oxford University Press), and peptide nucleic acid backbones and linkages (see Egholm (1992) *J. Am. Chem. Soc.* 114:1895; Meier et al. (1992) *Chem. Int. Ed. Engl.* 31: 1008; Nielsen (1993) *Nature,* 365: 566; Carlsson et al. (1996) *Nature* 380: 207). Other analog nucleic acids include those with positive backbones (Denpcy et al. (1995) *Proc. Natl. Acad. Sci. USA* 92: 6097; non-ionic backbones (U.S. Pat. Nos. 5,386,023, 5,637,684, 5,602,240, 5,216,141 and 4,469, 863; Angew. (1991) *Chem. Intl. Ed. English* 30: 423; Letsinger et al. (1988) *J. Am Chem. Soc.* 110:4470; Letsinger et al. (1994) *Nucleoside & Nucleotide* 13:1597; Chapters 2 and 3, ASC Symposium Series 580, "Carbohydrate Modifications in Antisense Research", Ed. Y. S. Sanghui and P. Dan Cook; Mesmaeker et al. (1994), *Bioorganic & Medicinal Chem. Lett.* 4: 395; Jeffs et al. (1994) *J. Biomolecular NMR* 34:17; *Tetrahedron Lett.* 37:743 (1996) and non-ribose backbones, including those described in U.S. Pat. Nos. 5,235,033 and 5,034,506, and Chapters 6 and 7, ASC Symposium Series 580, *Carbohydrate Modifications in Antisense Research*, Ed. Y. S. Sanghui and P. Dan Cook. Nucleic acids containing one or more carbocyclic sugars are also included within the definition of nucleic acids (see Jenkins et al. (1995), *Chem. Soc. Rev.* pp 169-176). Several nucleic acid analogs are described in Rawls, C & E News Jun. 2, 1997 page 35. These modifications of the ribose-phosphate backbone may be done to facilitate the addition of additional moieties such as labels, or to increase the stability and half-life of such molecules in physiological environments. As used herein, oligonucleotide is substantially equivalent to the terms "amplimers", "primers", "oligomers", and "probes", as commonly defined in the art.

The terms "complementary" or "complementarity", as used herein, refer to the natural binding of polynucleotides under permissive salt and temperature conditions by base-pairing. For example, the sequence "A-G-T" binds to the complementary sequence "T-C-A". Complementary between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands and in the design and use of PNA molecules.

The term "hybridization", as used herein, refers to any process by which a strand of nucleic acid binds with a complementary strand through base pairing.

The term "hybridization complex", as used herein, refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0$ t or $R_0$ t analysis) or between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

As used herein a "dominant negative mutant" refers to a gene product that adversely affect the normal, wild-type gene product within the same cell. A dominant negative mutant may still interact with similar elements as the wild type product but blocks some aspect of its function. When used in reference to a transcription factor, enzyme or other bioactive protein, the dominant negative mutant can bind to its native substrate but fails to include the activation function. As discussed herein, the dominant negative mutant of β-TrCP (β-TrCP2$^{\Delta N}$) may bind to its native substrate but fails to effect phosphorylation of the substrate, in particular, serine 662 of the Gli2 peptide.

The Invention

A model system for screening and identification of compounds that interfere with Gli2 dependent tumorigenesis and provide potential use as anticancer agents is provided. In particular, the invention includes a Gli2 protein having an S662A point mutation that interferes with binding by the ubiquitin-ligase β-TrCP. The mutation inhibits Gli2 degradation by the ubiquitin pathway. Gli2 stability and half-life are increased in the host cell resulting in an increase in Gli2-dependent transcription and concomitant neoplasia and tumorigenesis. Expression of the Gli2 mutant allows for the high throughput screening of compounds that interfere with the tumorigenesis thereby identifying anticancer agents.

Therefore, in one exemplary embodiment, the invention includes an isolated polypeptide having the sequence set forth in SEQ ID NO: 2, comprising the Gli2$^{S662A}$ mutant. In some embodiments, the invention includes a host cell, the genome of which is augmented with the nucleic acid molecule encoding the amino acid sequence set forth in SEQ ID NO:6In still other exemplary embodiments the invention further includes an isolated polynucleotide having the sequence set forth in SEQ ID NO: 5 or conservative variations thereof wherein the polynucleotide codes for the expression of an amino acid sequence as set forth in SEQ ID NO:6.

In another exemplary embodiment, the invention includes an isolated polypeptide coding for the Gli2 transcription factor set forth in SEQ ID NO:6, wherein the β-TrCP2 binding motif DSGV/M is mutated to $Xaa_1Xaa_2Xaa_3Xaa_4$, wherein $Xaa_1$ represents any amino acid except aspartic acid, $Xaa_2$ represents any amino acid except for serine, $Xaa_3$ represents any amino acid except for glycine and $Xaa_4$ represents any amino acid except valine or methionine such that Gli2 no longer binds β-TrCP2. Further, in some aspects according to the invention, the invention further includes a host cell comprising a genome which is augmented with a nucleic acid molecule encoding the polypeptide see forth in SEQ ID NO:6 wherein the DSGV/M binding motif is disrupted. In still other aspects, the invention further includes an isolated polynucleotide coding for a Gli2 polypeptide having a disrupted β-TrCP2 binding motif.

In still another exemplary embodiment the invention includes a bioassay for evaluating the efficacy of anticancer agents. In this embodiment, the invention comprises:
(a) culturing cells which contain non-endogenous DNA which expresses a Gli2$^{S662A}$ protein having the sequence set forth in SEQ ID NO:6 SEQ ID NO: 2;
(b) expressing the non-endogenous DNA in the cultured cells;
(c) identifying the transformation to a neoplastic state of the cells;
(d) assaying for compounds that inhibit or ameliorate the transformation to a neoplastic state;
thereby evaluating the efficacy of anticancer agents.

In some versions, this embodiment further includes a reporter plasmid wherein the reporter plasmid includes one or more copies of 3' Gli binding sites and where binding of the Gli2 to the binding site results in expression of a reporter gene. In various exemplary embodiments, the bioassay further includes a reporter gene. In various exemplary embodiments, the reporter gene may comprise luciferase, β galactosidase, green fluorescent protein or combinations thereof.

In still other exemplary embodiments, the invention includes a bioassay for identifying inhibitors of the hedgehog signaling pathway comprising:
(a) culturing cells which contain non-endogenous DNA which expresses a Gli2$^{S662A}$ protein having the sequence set forth in SEQ ID NO:5;
(b) expressing the non-endogenous DNA in the cltured cells;
(c) identifying an increase in the hedgehog signaling pathway;
(d) contacting the cells with a compound that inhibits the increase in the hedgehog cascade;
thereby identifying inhibitors of the hedgehog signaling pathway.

In still other preferred embodiments, the invention includes an expression vector encoding the isolated polypeptide of SEQ ID NO. 2, operatively linked to a promoter. In some embodiments, the promoter is an inducible promoter. However, in still other embodiments, the promoter is a constitutive promoter.

Example 1

General Experimental Procedures

DNA Constructs: The pcDNA3.1-Flag-Gli2 plasmid (FIG. 1A) was generated using full-length mouse Gli2 mRNA having the sequence set forth in SEQ ID NO: 1 and having the GenBank accession number NM$_{001081125}$ and coding for the Gli2 protein as set forth in GenBank Accession No. NP$_{001074594}$ and provided by Drs. Hiroshi Sasaki and Chi-ching Hui (Sasaki, H., Nishizaki, Y., Hui, C., Nakafuku, M., and Kondoh, H. (1999) Development 126, 3915-3924). Replacement of serine 662 with alanine, for the protein sequence as set forth in SEQ ID NO: 6 was carried out using a site-directed mutagenesis kit sold under the trade name QUICKCHANGE SITE-DIRECTED MUTAGENESIS KIT (Stratagene). The cDNA encoding the S662A point mutant was created using primers: 5' GCC CCC AAC AAT GAC GCC GGC ATG GAG ATG CCG 3' (primer3, SEQ ID NO: 3) and 5' CGG CAT CTC CAT GCC GGC GTC ATT GTT GGG GGC 3' (primer4, SEQ ID NO: 4,) resulting in the sequence set forth in SEQ ID NO: 5, mutating the serine codon, AGT to the alanine codon GCC at residues 2333-2335 (wt) which correspond to residues 1984-1986 of the insert. As shown in FIG. 1B, the underlined residues in the primers 3 and 4 represent the nucleotide changes resulting in S662A point mutation. The sequence for the wild-type insert is given in SEQ ID NO: 2. HA-tagged β-TrCP2 and β-TrCP2$^{ΔN}$ encoding plasmids, the constructs for specific knock down of β-TrCP2 (shBTR2), β-TrCP1 (shBTR1), as well as control shRNA construct (shCON) (Kumar, K. G., Tang, W., Ravindranath, A. K., Clark, W. A., Croze, E., and Fuchs, S. Y. (2003) Embo J 22, 5480-5490) were generously provided by Dr. S. Y. Fuchs (Fuchs, S. Y., Chen, A., Xiong, Y., Pan, Z. Q., and Ronai, Z. (1999) Oncogene 18, 2039-2046). 8x3'Gli BS-LucII [8 directly repeated copies of 3'Gli binding site from HNF3β floor plate enhancer cloned into p851LucII (Sasaki, H., Hui, C., Nakafuku, M., and Kondoh, H. (1997) Development 124, 1313-1322) was a gift of Dr. H. Sasaki (Osaka University, Osaka, Japan), K17-luc (K17 driven luciferase reporter) was from Dr. P. Coulombe, pGL3-Bc12 promoter luciferase plasmid (pGL3 basic vector with 1.9 kb of the putative promoter and 5' untranslated region of human Bc12) was generously provided by Dr. F. Aberger (Regl, G., Kasper, M., Schnidar, H., Eichberger, T., Neill, G. W., Philpott, M. P., Esterbauer, H., Hauser-Kronberger, C., Frischauf, A. M., and Aberger, F. (2004) Cancer Res 64, 7724-7731). Plasmids for expression of renilla luciferase (pRL-TK) and β-galactosidase (pSV-40 β-gal) were purchased (Promega Corp., Madison, Wis.).

Tissue Culture and Transfections: 293T human embryo kidney cells and HeLa human cervical adenocarcinoma cells were purchased from ATCC (Manassas, Va., Catalog #CRL-11268). Cells were grown in DMEM in the presence of 10% fetal bovine serum (FBS) and antibiotics at 37.degree. C. and 5% CO.sub.2. Transfections were performed using the calcium phosphate procedure or lipofection with a lipofection kit sold under the trade name LIPOFECTAMINE 2000 (Invitrogen, Carlsbad, Calif.).

Antibodies and Western Blotting: Antibodies against HA (Roche), Gli2, β-actin (Santa Cruz Biotechnology), the M2 protein sold under the trademark FLAG M2 (Sigma-Aldrich) were purchased. β-TrCP antibody was described previously (Spiegelman, V. S., Tang, W., Katoh, M., Slaga, T. J., and Fuchs, S. Y. (2002) Oncogene 21, 856-860, hereby incorporated by reference in its entirety). Horseradish peroxidase conjugated secondary antibodies were purchased (Cell Signaling, Santa Cruz, Jackson). Immunoprecipitation and immunoblotting procedures were performed as described elsewhere (34).

In vivo Binding Assay: 293T cells co-transfected with FLAG-tagged Gli2 or Gli2$^{S662A}$ and HA-tagged β-TrCP2 were lysed in RIPA lysis buffer. Interaction between the expressed proteins was assessed by immunoprecipitation with FLAG or HA antibodies and immunoblotting with HA or FLAG antibodies, respectively. The interaction between endogenous proteins in the protein lysates from HeLa cells was analyzed by immunoprecipitation with Gli2 antibody and immunoblotting with β-TrCP antibody.

In vitro Binding Assay: Recombinant Gli2 proteins expressed in 293T cells were immunopurified with Flag antibody and protein A/G agarose beads, stringently washed with stripping buffer containing 20 mM Tris HCl (pH 7.5), 1M NaCl, 50 mM NaF, and 0.1% Nonidet P40 and equilibrated with binding buffer (20 mM Tris HCl, pH 7.5, 100 mM NaCl, 50 mM NaF, and 0.1% Nonidet P40). For treatment with phosphatase λ, the beads were washed with the binding buffer without phosphatase inhibitors and incubated with the phosphatase λ, for 1 h at 37° C. followed by washes in stripping buffer and re-equilibration with binding buffer. Flag-Gli2 proteins immobilized on the beads were incubated with in vitro-translated and $^{35}$S-labeled β-TrCP2 for 60 min at 4° C. The beads were extensively washed with binding buffer and associated proteins were analyzed by SDS-PAGE and autoradiography.

S$^{35}$ labeled β-TrCP2 was synthesized in vitro using TnT kit (Promega). Lysates of 293T cells transfected with FLAG Gli-2 and Gli-2$^{S662A}$ were incubated with S35 labeled β-TrCP2 for 3 hrs at 4° C. These lysates were immunoprecipitated with FLAG antibody and associated proteins were analyzed by SDS-PAGE and autoradiography.

In vivo Ubiquitination Assay: 293T cells were co-tranfected with HA-tagged ubiquitin, HA-tagged βTrCP2 and Flag-tagged Gli2 or Gli2$^{S662A}$. Cells were lysed in RIPA lysis buffer and immunoprecipitated with FLAG antibody. Immunocomplexes were analyzed by SDS-PAGE and immunoblotting with HA antibody.

Degradation Assay: Pulse chase analysis was carried out on 293T cells as described elsewhere (DasGupta, R., and Fuchs, E. (1999) *Development* 126, 4557-4568, hereby incorporated by reference in its entirety). Briefly, cells were grown in 100 mm dishes and transfected with the indicated plasmids. Cells were starved in methionine and cysteine free DMEM followed by metabolically labeling with a $^{35}$S-methionine/$^{35}$S-cysteine mixture (Perkin Elmer, Inc.). Chase was performed in complete DMEM (10% FBS) supplemented with 2 mM unlabeled methionine and cysteine and cells were harvested at respective time points. Gli2 proteins were immunoprecipitated from RIPA lysates with FLAG antibody, separated by SDS-PAGE and analyzed by autoradiography.

Luciferase Reporter Assays: Hela cells were transfected with 8×3'Gli BS-LucII reporter, K17 luciferase reporter plasmid, or pGL3-Bcl2promo luciferase reporter plasmid and respective Gli2 expression plasmids. Luciferase activity was estimated using Luciferase Reporter Assay Reagent (Promega). β-galactosidase was used for normalization and estimated using β-gal assay reagent (Pierce Biotechnology).

Immunohistochemistry: Prostate tissue arrays were purchased (Cybrdi, Inc., Frederick, Md.). Sections were incubated at 4° C. overnight with Gli-2 G20 antibody followed by donkey anti-goat biotin secondary antibody, ABC reagent (Vector Laboratories, Burlingame, Calif.) and developed by DAB (Sigma-Aldrich).

RNA isolation and Real-Time RT PCR: Real Time RT PCR for quantitative RNA measurements of gli2 were done using SYBR Green PCR Core reagents (Applied Biosystems) as described before (Lamm 2002). GAPDH was used as reference gene.

Example 2

β-TrCP2 Interacts with Gli2, and Promotes its Ubiquitination In Vivo

SCF$^{β-TrCP}$ ubiquitin ligase recognizes DSG(X)$_{2+n}$S destruction motif to target proteins for ubiquitination and further degradation (reviewed in (23)). Therefore, the inventors designed a series of experiments to investigate the potential interatction of Gli2 with ligases responsible for ubiquitination and degradation of target molecules.

Sequence analysis of Gli2 revealed the DSGV/MEMPGT-GPGS motif, which is conserved among various mammalian species (FIG. 2A). The inventors analyzed whether substrate recognizing component of SCF$^{beta-TrCP}$ ubiquitin ligase, F-box protein β-TrCP2 interacts with Gli2. The inventors found that exogenously expressed Gli2 and β-TrCP2 (FIG. 2B), as well as endogenous proteins (FIG. 2C) interact in vivo in co-immunoprecipitation assay. Gli2 was also shown to bind in vitro translated β-TrCP2 protein (FIG. 2D). To determine whether the putative β-TrCP recognition motif is responsible for this interaction, the inventors substituted potentially phosphorylated Serine 662 to Alanine in this motif of Gli2 (FIGS. 1B, 2A). This single amino acid substitution is predicted to disrupt Gli2 interactions with β-TrCP. Indeed, in both assays, Gli2$_{S662A}$ (SEQ ID NO:6) binding to β-TrCP2 was greatly diminished (FIGS. 2B and D). Treatment of Flag-Gli2 with protein phosphatase X abolished the ability of Gli2 to bind β-TrCP2 in vitro (FIG. 2D). These results demonstrate that phosphorylation of Gli2 is necessary for its recognition by β-TrCP ubiquitin ligase receptor. Thus, these data indicate that disruption of Gli2/β-TrCP2 binding, by mutation of any of the residues in the DSGX motif will affect the ubiquitination of Gli2, resulting in stabilization of the Gli2 protein and increased Gli2 dependent transcription.

Interaction of β-TrCP2 with specific substrates results in ubiquitination of these proteins. Co-transfection of cells with the β-TrCP2 construct accelerated the ubiquitination of wild type Gli2 (FIG. 2E, Lane 3) as measured by in vivo ubiquitination assay. In contrast, the ubiquitination of the Gli2$^{S662A}$ mutant that interacts poorly with β-TrCP2 was less efficient, and was not affected by β-TrCP2 over-expression (FIG. 2E, Lane 6). These data demonstrate that DSGX motif is indeed the β-TrCP2 binding site, that substitution of residues within the motif inhibits binding of β-TrCP2 and that serine 662 is critical for the interaction between Gli2 and β-TrCP2, and that binding to β-TrCP is important for Gli2 ubiquitination.

Example 3

Inhibition of β-TrCP Function Stabilizes Gli2 Protein

In order to analyze the role of β-TrCP in the degradation of Gli2, the inventors inhibited β-TrCP activity by either knocking down the expression of β-TrCP1 and β-TrCP2 proteins by using short hairpin RNA (shRNA) or by expression of dominant negative mutant of β-TrCP (βTrCP2$^{ΔN}$) (Fuchs, S. Y., Chen, A., Xiong, Y., Pan, Z. Q., and Ronai, Z. (1999) *Oncogene* 18, 2039-2046).

Figure 3:
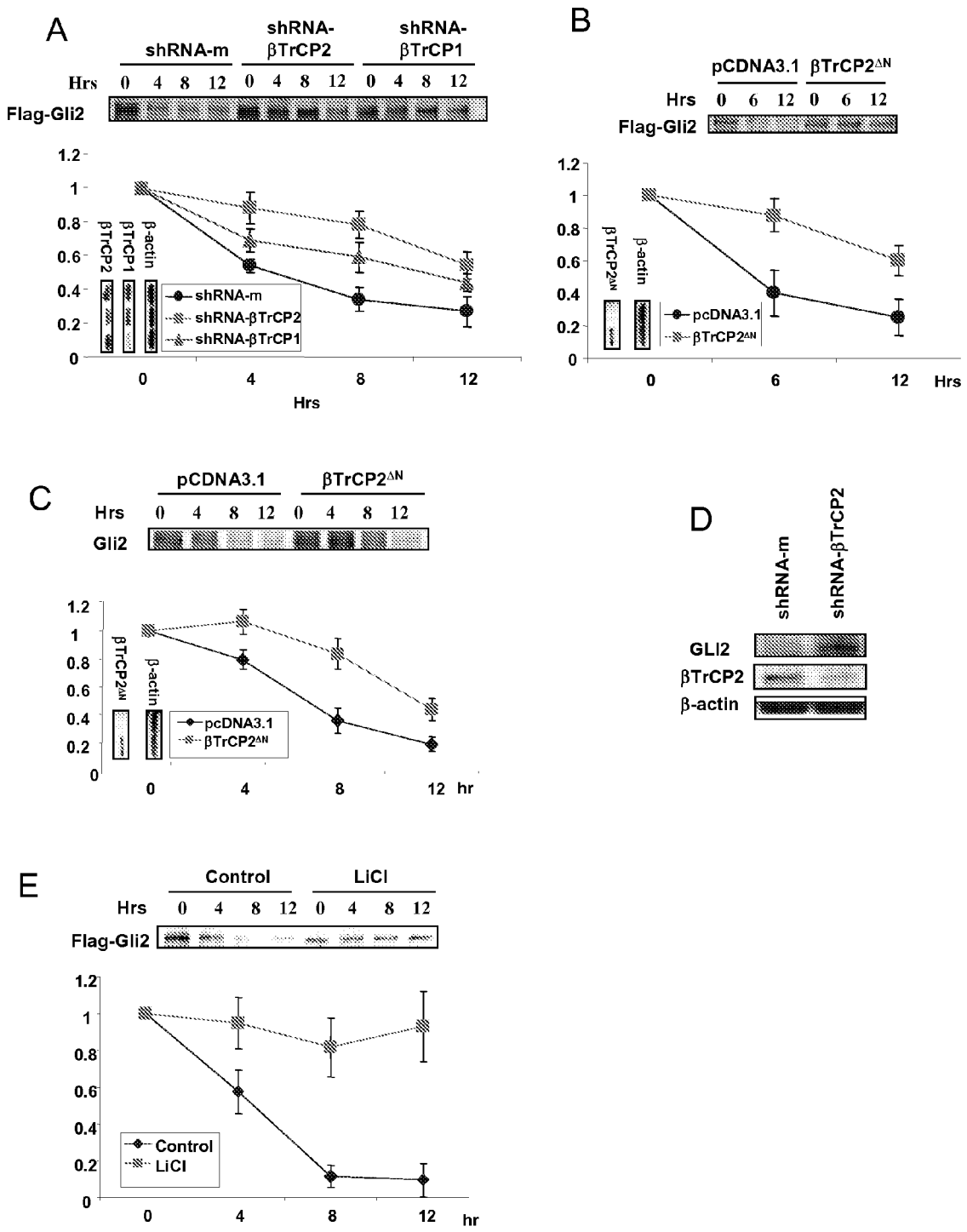
FIGS. 3A-3E, are data illustrating that inhibition of the β-TrCP ligase stabilizes the Gli2 protean.

In these experiments, 293T cells were transfected with Flag-Gli2$^{wt}$ in the presence of the indicated shRNA constructs. Pulse chase analysis of Flag-Gli2 degradation in 293T cells was performed with metabolically labeled with $^{35}$S-methionine/$^{35}$S-cysteine. Cells were harvested at different time points of chase with unlabeled methionine and cysteine. Gli2 was immunoprecipitated with Flag antibody and analyzed using autoradiography. The levels of β-TrCP1 and β-TrCP2 expression in 293T cells transfected with the indicated shRNA analyzed by immunoblotting was also determined (FIG. 3A). The inventors also performed a pulse chase analysis of Flag-Gli2$^{wt}$ protein expressed in 293T cells with or without dominant negative HA-tagged β-TrCP2$^{\Delta N}$ mutant and analyzed as in FIG. 3A. The levels of HA-β-TrCP2$^{\Delta N}$ expression in 293T cells transfected was analyzed by immunoblotting with HA antibody (FIG. 3B). Further, a pulse chase analysis of endogenous Gli2 protein in 293T cells with or without dominant negative HA-tagged β-TrCP2$^{\Delta N}$ mutant. 293T cells were metabolically labeled with $^{35}$S-methionine/$^{35}$S-cysteine. The cells were and harvested at different time points of chase with unlabeled methionine and cysteine. Gli2 was immunoprecipitated with Gli2 antibody (Santa Cruz Biotechnology) and analyzed using autoradiography. The levels of HA-β-TrCP2$^{\Delta N}$ expression in 293T cells transfected was analyzed by immunoblotting with HA antibody (FIG. 3C). In this series of experiments, the expression of endogenous GLI2 protein in 293T cells transfected with indicated shRNA constructs was analyzed by immunoblotting with GLI2 antibody (FIG. 3D). Finally, pulse chase analysis of Flag-Gli2$^{wt}$ protein expressed in 293T cells treated with LiCl was analyzed as in FIG. 3A. Cells were serum starved for 12 hr and then treated with 40 mM LiCl 1 hr prior to the chase (FIG. 3E).

The results of the above experiments show that inhibition of β-TrCP function leads to stabilization of Gli2 protein (FIG. 3A-C). β-TrCP2$^{\Delta N}$ extends the half-life of Gli2 from about 6 to 12 hours. Interestingly, shRNA against β-TrCP2 appeared to be more effective in the inhibition of Gli2 turnover than β-TrCP1 specific shRNA (FIG. 3A). Importantly, inhibition of β-TrCP function resulted in stabilization (FIG. 3C) and accumulation (FIG. 3D) of endogenous Gli2 in 293T cells. These data suggest that β-TrCP is involved in degradation of Gli2 protein in mammalian cells.

Although the kinase responsible for Gli2 phosphorylation within β-TrCP recognition motif is not known, phosphorylation of *Drosophila* Ci by shaggy (*Drosophila* homologue of GSK-3β) was demonstrated to be a necessary step in Ci proteolysis. Recently Gli2 was shown to be phosphorylated by GSK3β. Treatment of cells with GSK3 inhibitor, LiCl substantially increased the half-life of Gli2 protein (FIG. 3E). These data suggest that GSK3 may be involved in phosphorylation-dependent degradation of Gli2.

Example 4

Figure 4:
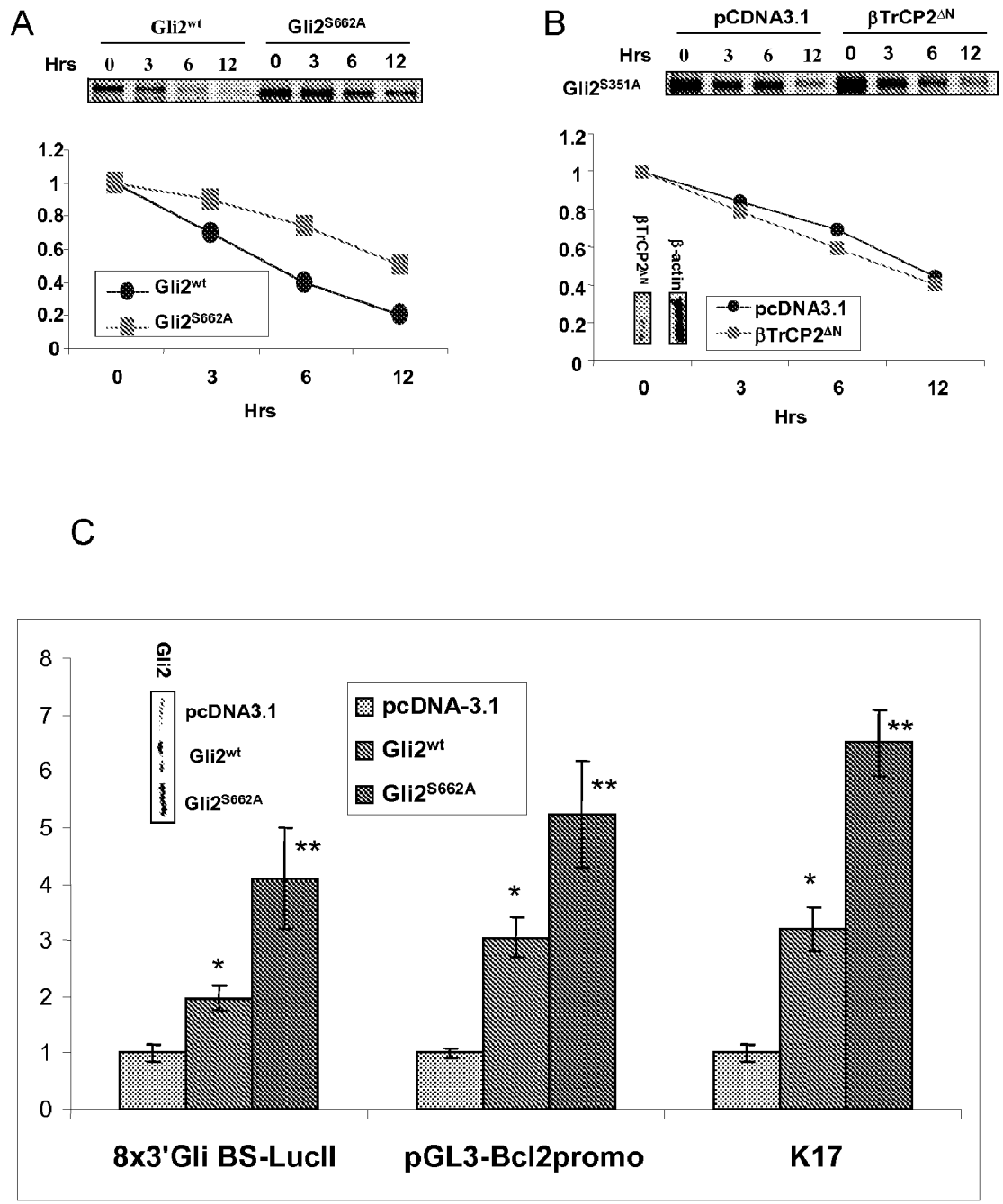

Gli2$^{S662A}$ is Expressed in Higher Levels and is More Potent in the Activation of Gli-Dependent Transcription than Gli2$^{wt}$ To further confirm the role of β-TrCP in proteolysis of Gli2, the inventors compared the rate of degradation Gli2$^{wt}$ with that of Gli2$^{S662A}$ mutant. In these experiments, Flag-Gli2 proteins (wild type or S662A mutant) were expressed in 293T cells and their degradation analyzed as in Example 3 (FIG. 4A). Also, a pulse chase analysis of Flag-Gli2$^{S662A}$ protein expressed in 293T cells was performed with or without dominant negative β-TrCP2$^{\Delta N}$ mutant and analyzed as in Example 3. The levels of HA-β-TrCP2$^{\Delta N}$ expression in 293T cells transfected was analyzed by immunoblotting with HA antibody (FIG. 4B). Further, HeLa cells were transfected with Gli-luciferase (8×3'Gli BS-LucII), pGL3-Bcl2promo luciferase, or K17 luciferase, and respective Gli2 expression plasmids as indicated (FIG. 4C). Luciferase activity was estimated using the Luciferase Reporter Assay Reagent (Promega, Madison, Wis.). β-galactosidase was used for normalization and estimated using β-gal assay reagent (Pierce Biotechnology, Rockford, Ill.). The levels of Flag-Gli2 expression in HeLa cells transfected with Flag-Gli2$^{wt}$ or Flag-Gli2$^{S662A}$ was analyzed by immunoblotting with Gli2 G-20 antibody with protein loading normalized by β-galactosidase activity FIG. 4C).

Gli2$^{S662A}$ poorly interacts with β-TrCP2 (FIGS. 2B, C), and is not ubiquitinated by β-TrCP2 (FIG. 3D). In comparison to Gli2$^{wt}$, Gli2$^{S662A}$ mutant protein is more stable and exhibits a half-life of more than 9 hours (FIG. 4A). Furthermore, over expression of dominant negative mutant of β-TrCP (β-TrCP2$^{\Delta N}$) did not affect the stability of Gli2$^{S662A}$ (FIG. 4B). These data demonstrate that serine 662 is critical for the interaction between Gli2 and β-TrCP2. Disruption of the DSGX motif by mutation of the serine residue renders it poorly interactive with β-TrCP, hence stabilizing the Gli2$^{S662A}$ mutant protein.

Stabilization of Gli2$^{S662A}$ mutant translates into the higher level of protein expression as compared to the wild type Gli2 (FIG. 4C, insert). HeLa cells transfected with the same amount of appropriate plasmids express higher level of Gli2$^{S662A}$ mutant protein as compared to the wild type protein. FIG. 4C demonstrates that Gli2$^{S662A}$ mutant is significantly more effective than Gli2$^{wt}$ in the activation of Gli-dependent transcriptional activity. 8×3'Gli BS-LucII, pGL3-Bcl2promo luciferase or K17 driven luciferase were utilized to measure Gli2 dependent transcriptional activation driven by Gli2$^{wt}$ or Gli2$^{S662A}$. Gli2$^{S662A}$ is about twice as potent, as Gli2$^{wt}$ in activation of transcription as measured by these 3 different reporter constructs. These results demonstrate that elevated Gli2 dependent transcriptional output is likely attributed to the higher levels of Gli2$^{S662A}$ protein expression. These data strongly suggest that Gli2 protein turnover is an important step in the modulation of Gli2 dependent transcription.

Gli transcription factors, including Gli1, Gli2 and Gli3, are the key modulators of Hh signaling. Gli2 and Gli3 contain both the amino terminal repressor domain as well as carboxyl terminal activator domain, whereas, Gli1 is comprised of only the carboxyl terminal activator domain. Hence, Gli1 acts as the transcriptional activator and is a secondary target, downstream of Gli2/Gli3. On the other hand, Gli3 is suggested to primarily act as the repressor, although, activator function for Gli3 has also been reported. Gli2, however, has been suggested to be the primary activator of Hh signaling. Mice homozygous for Gli2 mutations exhibit developmental defects and over expression of Gli2 results in formation of BCCs.

It has been previously shown that β-TrCP targets several essential proteins in cell transformation and signal transduction for ubiquitination and degradation, including IκBα, β-catenin and ATF4 proteins. Genetic evidence suggest that *Drosophila* Slimb F box protein is involved in Hh signaling pathway in processing of full length Ci155 protein to truncated repressor form Ci75. As disclosed and shown herein, Gli2 is the substrate of β-TrCP for ubiquitination and degradation. However, unlike Ci, there is no evidence suggesting that Gli2 undergoes proteolytic cleavage. The inventors were unable to detect any smaller protein species of Gli2 indicating that Gli2 protein stabilization, rather than inhibition of processing, is important for downstream signaling.

Example 5

GLI2 is Over-Expressed in Prostate Cancer Cells

Figure 5:
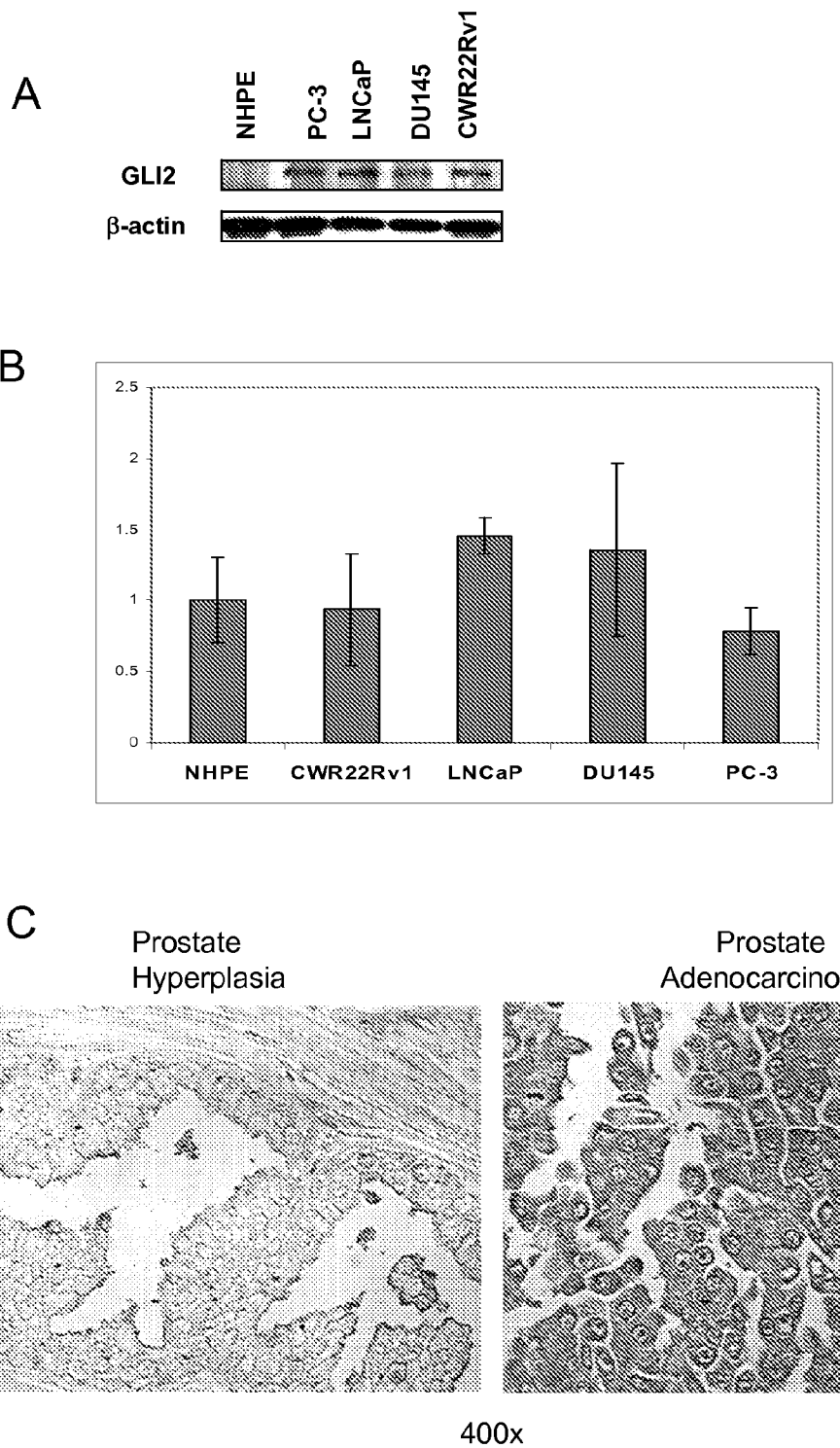
FIGS. 5A-C, FIG. 5A shows an immunoblot of GLI2 expression prostate cancer cells using Gi2 antibody (G20). A representative of two independent experiments is shown.

Overexpression of Gli2 in transgenic mice induces formation of BCCs (Grachtchouk, M., Mo, R., Yu, S., Zhang, X., Sasaki, H., Hui, C. C., and Dlugosz, A. A. (2000) *Nat Genet* 24, 216-217), and GLI2 mRNA is upregulated in the majority of human BCCs. However, there are no reports examining the expression of GLI2 protein in human cancers. Thus, the inventors examined the expression of GLI2 in a panel of cancer cell lines. Levels of GLI2 expression in prostate cancer cell lines were analyzed using immunoblotting with Gli2 antibody (G20) as shown in FIG. 5A. GLI2 mRNA expression was also assessed by Real Time RT-PCR as shown in FIG. 5B. Finally, a human prostate cancer tissue array was immunostained with GLI2 (G20) for expression of GLI2 full length protein.

The results of the above described experiments show that GLI2 protein is dramatically induced in prostate cancer cell lines as compared to normal human prostate epithelial (NHPE) cells (FIG. 5A). On the other hand, there is no significant difference in the expression of GLI2 mRNA in these cells (FIG. 5B). These data are in line with previous observations that elevated expression of Gli2 message is a rare event in human prostate tumors and cell lines. In all, this data suggests that a novel post-transcriptional mechanism, most likely protein stabilization, is responsible for high levels of GLI2 expression in prostate cancer cells. Constitutive activation of Hh signaling in prostate cancer has been recently reported (Karhadkar, S. S., Steven Bova, G., Abdallah, N., Dhara, S., Gardner, D., Maitra, A., Isaacs, J. T., Berman, D. M., and Beachy, P. A. (2004) *Nature* 431, 707-712). The data disclosed herein demonstrates that high levels of GLI2 protein expression strongly correlate with Hh pathway activation in cancer cells, suggesting that GLI2 plays an important role in mediation of Hh signaling in cancer and especially in prostate cancer cells. Immunohistochemical analysis of an array of primary human prostate tumors using GLI2 antibody that recognizes C-terminus of GLI2 protein revealed high levels expression of GLI2 in the majority of malignant prostate epithelial cells as compared to the benign ones. Nuclear localization of GLI2 protein is a hallmark of its transcriptional activity. Importantly, 26 out of 29 prostate adenocarcinomas (90%) exhibited strong nuclear or nuclear-cytoplasmic staining as shown in Table 1. In contrast, only one out of 5 prostate hyperplasia samples (20%) revealed nuclear accumulation of GLI2. FIG. 5C shows a representative GLI2 immuno-staining of malignant and benign prostate tissues. These data further substantiate the importance of GLI2 over expression and activation in prostate cancer development, supporting indicating that GLI2 may be a key component in Hh pathway activation in prostate cancer. Future studies will define the role of GLI2 in prostate tumorigenesis, and delineate the mechanisms by which prostate cancer cells achieve stabilization of GLI2.

TABLE 1

Gli2 expression in Human Prostate Carcinoma and Hyperpalsia

| SAMPLE | AGE | SEX | ORGAN | PATHOLOGY DIAGNOSIS | GLI2 NUCLEAR EXPRESSION |
|---|---|---|---|---|---|
| 1 | 78 | M | Prostate | Adenocarcinoma Grade II | + |
| 2 | 66 | M | Prostate | Adenocarcinoma Grade III | + |
| 3 | 60 | M | Prostate | Adenocarcinoma Grade II/III | + |
| 4 | 67 | M | Prostate | Adenocarcinoma Grade II | + |
| 5 | 69 | M | Prostate | Adenocarcinoma Grade I | + |
| 6 | 70 | M | Prostate | Adenocarcinoma Grade III | + |
| 7 | 76 | M | Prostate | Adenocarcinoma Grade III | + |
| 8 | 63 | M | Prostate | Adenocarcinoma Grade III | + |
| 9 | 87 | M | Prostate | Adenocarcinoma Grade III | − |
| 10 | 80 | M | Prostate | Adenocarcinoma Grade II | + |
| 11 | 78 | M | Prostate | Adenocarcinoma Grade III | + |
| 12 | 69 | M | Prostate | Adenocarcinoma Grade I | + |
| 13 | 70 | M | Prostate | Adenocarcinoma Grade III/II | + |
| 14 | 60 | M | Prostate | Adenocarcinoma Grade I | + |
| 15 | 70 | M | Prostate | Adenocarcinoma Grade I/II | + |
| 16 | 82 | M | Prostate | Adenocarcinoma Grade III | + |
| 17 | 75 | M | Prostate | Adenocarcinoma Grade III | + |
| 18 | 81 | M | Prostate | Adenocarcinoma Grade III | + |
| 19 | 72 | M | Prostate | Adenocarcinoma Grade III | + |
| 20 | 85 | M | Prostate | Adenocarcinoma Grade I | + |
| 21 | 80 | M | Prostate | Adenocarcinoma Grade II | + |
| 22 | 89 | M | Prostate | Adenocarcinoma Grade III | + |
| 23 | 64 | M | Prostate | Adenocarcinoma Grade III | + |
| 24 | 73 | M | Prostate | Adenocarcinoma Grade III | + |
| 25 | 65 | M | Prostate | Hyperplasia | − |
| 26 | 64 | M | Prostate | Adenocarcinoma Grade III | + |
| 27 | 75 | M | Prostate | Adenocarcinoma Grade II | + |
| 28 | 78 | M | Prostate | Adenocarcinoma Grade III | + |
| 29 | 60 | M | Prostate | Adenocarcinoma Grade III | − |
| 30 | 73 | M | Prostate | Adenocarcinoma Grade II | − |
| 31 | 72 | M | Prostate | Hyperplasia | +/− |
| 32 | 63 | M | Prostate | Hyperplasia | − |
| 33 | 75 | M | Prostate | Hyperplasia | − |

The foregoing data show that elevated levels of Gli2 are present in neoplastic cells. Further, the inventors have shown that by using a Gli2$^{S662A}$ mutant physiologically active Gli2 can be expressed that does not bind the β-TRCP ubiquitin ligase. Further, without being held to any particular theory, increased levels of Gli2 are indicative of a neoplastic fate.

Therefore, expression of physiologically active Gli2 allows investigators to induce neoplastic activity in cell preparations and provides a model by which drugs and/or other chemical compositions can be used to modulate the fate of the preparations. In such models, the ability of Gli2 to transduce signals in the Hh pathway the ultimately lead to malignant states can be investigated and provide clues to the efficacy of treatments interrupting the Gli2/Hh pathway.

While this invention has been described in conjunction with the various exemplary embodiments outlined above, various alternatives, modifications, variations, improvements and/or substantial equivalents, whether known or that are or may be presently unforeseen, may become apparent to those having at least ordinary skill in the art. Accordingly, the exemplary embodiments according to this invention, as set forth above, are intended to be illustrative, not limiting. Various changes may be made without departing from the spirit and scope of the invention. Therefore, the invention is intended to embrace all known or later-developed alternatives, modifications, variations, improvements, and/or substantial equivalents of these exemplary embodiments. All publications, patents, and patent applications cited herein are hereby incorporated by reference in their entirety for all purposes.

---

What is claimed is:

1. An in vitro host cell comprising a genome which is augmented with an isolated nucleic acid molecule encoding a Gli2 transcription factor having the amino acid sequence set forth in SEQ ID NO:6.

2. An isolated polynucleotide wherein the polynucleotide codes for a polypeptide having the sequence set forth in SEQ ID NO:6.

3. An expression vector comprising a nucleic acid sequence encoding the isolated polypeptide of SEQ ID NO:6, wherein the nucleic acid sequence is operatively linked to a promoter.

4. The expression vector of claim 3, wherein the promoter is an inducible promoter.

5. The expression vector of claim 3, wherein the promoter is a constitutive promoter.

* * * * *

SEQUENCE LISTING

```
<160> NUMBER OF SEQ ID NOS: 13

<210> SEQ ID NO 1
<211> LENGTH: 6708
<212> TYPE: DNA
<213> ORGANISM: Mus musculus
<220> FEATURE:
<221> NAME/KEY: CDS
<222> LOCATION: (350)..(4981)

<400> SEQUENCE: 1
aatgagactt cgaggaggag cgggaggcgg cggcggcggc tacagaggac gcggaggaag      60
gcgaggagga gccagaggaa ggagcacggg tcgtgcgtag catcgcagcc gcccggagct     120
gctggcctgg tgtccttagg gactgcccga gtccccgcc cgccttggtc ccctcctctg     180
cctggccagc cccgccccgg cagccggagc ccccgcactc ggcagcccca ctccagccaa     240
gttgggatgg ggccctgcaa ccactgcccg gcgcccgaga ggccacctgc atgctagagg     300 caaactttg tctcctcggg tccgccacca aagagtatga gcctctgag atg gag act     358
                                                        Met Glu Thr
                                                          1 tct gcc cca gcc cct gca ctg gag aag aaa gaa gcc aag agt ggt ctc      406
Ser Ala Pro Ala Pro Ala Leu Glu Lys Lys Glu Ala Lys Ser Gly Leu
  5                  10                  15 ttg gag gac agc agc ttc ccc gac cca ggg aaa aag gcc tgt cct ctg      454
Leu Glu Asp Ser Ser Phe Pro Asp Pro Gly Lys Lys Ala Cys Pro Leu
 20                  25                  30                  35 gcg gtg gcc gca gct gta gcc gcc cac gga gtt cct cag cag ctc ctg      502
Ala Val Ala Ala Ala Val Ala Ala His Gly Val Pro Gln Gln Leu Leu
                 40                  45                  50 ccg gct ttc cac gcg cct ttg ccg att gac atg aga cac cag gag gga      550
Pro Ala Phe His Ala Pro Leu Pro Ile Asp Met Arg His Gln Glu Gly
                 55                  60                  65 agg tac cat tat gac cct cac tct gtc cac agt gta cac ggg cct ccc      598
Arg Tyr His Tyr Asp Pro His Ser Val His Ser Val His Gly Pro Pro
         70                  75                  80 acc cta agt ggc agc cct gtc atc tca gat atc tcc ttg ata cga ctt      646
Thr Leu Ser Gly Ser Pro Val Ile Ser Asp Ile Ser Leu Ile Arg Leu
     85                  90                  95 tct cca cac cct gct ggc cct gga gag tca ccc ttc agc gcc cac cac      694
Ser Pro His Pro Ala Gly Pro Gly Glu Ser Pro Phe Ser Ala His His
100                 105                 110                 115 ccc tac gtg aac ccc cat atg gag cac tac ctc cgg tct gtg cac agc      742
Pro Tyr Val Asn Pro His Met Glu His Tyr Leu Arg Ser Val His Ser
                120                 125                 130 agc ccc aca ctc tca atg atc tct gcc gcc agg ggc ctc agc cct gct      790
Ser Pro Thr Leu Ser Met Ile Ser Ala Ala Arg Gly Leu Ser Pro Ala
                135                 140                 145
```

```
gat gtg gcc cac gaa cat ctg aaa gag agg gga ctc ttt agc ctc gca        838
Asp Val Ala His Glu His Leu Lys Glu Arg Gly Leu Phe Ser Leu Ala
            150                 155                 160 gcc cca ggc acc aac cct tca gac tat tac cac cag atg acc ctc atg        886
Ala Pro Gly Thr Asn Pro Ser Asp Tyr Tyr His Gln Met Thr Leu Met
165                 170                 175 gca agc cac ccc acc cct tat ggg gac ctt cta atg cag agc ggg ggt        934
Ala Ser His Pro Thr Pro Tyr Gly Asp Leu Leu Met Gln Ser Gly Gly
180                 185                 190                 195 gct gct agc gca ccc cat ctc cat gac tac ctc aac cct gtg gat gca        982
Ala Ala Ser Ala Pro His Leu His Asp Tyr Leu Asn Pro Val Asp Ala
                200                 205                 210 tca cga ttc tct agt cca cgt gtg acc cca cga ctg agc cgc aag cgg       1030
Ser Arg Phe Ser Ser Pro Arg Val Thr Pro Arg Leu Ser Arg Lys Arg
            215                 220                 225 gct ctg tcc atc tcc ccg ctc tca gat gcc agc ctc gac cta caa cgc       1078
Ala Leu Ser Ile Ser Pro Leu Ser Asp Ala Ser Leu Asp Leu Gln Arg
230                 235                 240 atg att cgg acc tct ccc aac tcg ctg gta gct tac atc aac aac tcc       1126
Met Ile Arg Thr Ser Pro Asn Ser Leu Val Ala Tyr Ile Asn Asn Ser
245                 250                 255 agg agc agc tca gca gcc agt ggc tct tat gga cat ctg tct gct ggt       1174
Arg Ser Ser Ser Ala Ala Ser Gly Ser Tyr Gly His Leu Ser Ala Gly
260                 265                 270                 275 gcc ctc agc cca gcc ttc act ttt ccc cac ccc atc aat cct gtg gcc       1222
Ala Leu Ser Pro Ala Phe Thr Phe Pro His Pro Ile Asn Pro Val Ala
                280                 285                 290 tac cag cag atc ctg agc cag cag cgg ggc ctg ggc tca gcc ttt gga       1270
Tyr Gln Gln Ile Leu Ser Gln Gln Arg Gly Leu Gly Ser Ala Phe Gly
            295                 300                 305 cac aca cca ccc ctg atc cag cct tca ccc acc ttc ttg gcc cag cag       1318
His Thr Pro Pro Leu Ile Gln Pro Ser Pro Thr Phe Leu Ala Gln Gln
310                 315                 320 ccc atg act ctc acc tcc atc agc acc atg cct acc caa ctc agc agc       1366
Pro Met Thr Leu Thr Ser Ile Ser Thr Met Pro Thr Gln Leu Ser Ser
325                 330                 335 agt agc agc aac tgt cta aat gat gcc aac cag aac aag cag aac agc       1414
Ser Ser Ser Asn Cys Leu Asn Asp Ala Asn Gln Asn Lys Gln Asn Ser
340                 345                 350                 355 gag tca gct gtg agc agc acc gtg aac ccc atc acc att cat aag cgg       1462
Glu Ser Ala Val Ser Ser Thr Val Asn Pro Ile Thr Ile His Lys Arg
                360                 365                 370 agc aag gtc aag act gag gct gag ggc ctg cgt cca gca tcc ccg ctt       1510
Ser Lys Val Lys Thr Glu Ala Glu Gly Leu Arg Pro Ala Ser Pro Leu
            375                 380                 385 gga ctg aca cag gag cag ctg gcc gat ctc aag gaa gac ctg gac agg       1558
Gly Leu Thr Gln Glu Gln Leu Ala Asp Leu Lys Glu Asp Leu Asp Arg
390                 395                 400 gat gac tgt aag cag gag gcc gag gtg gtc atc tac gag acc aac tgc       1606
Asp Asp Cys Lys Gln Glu Ala Glu Val Val Ile Tyr Glu Thr Asn Cys
405                 410                 415 cac tgg gca gac tgc acc aag gag tat gac aca cag gag cag ctg gtg       1654
His Trp Ala Asp Cys Thr Lys Glu Tyr Asp Thr Gln Glu Gln Leu Val
420                 425                 430                 435 cat cat atc aac aat gaa cac atc cac ggg gag aag aag gag ttc gtg       1702
His His Ile Asn Asn Glu His Ile His Gly Glu Lys Lys Glu Phe Val
                440                 445                 450 tgc cgc tgg cag gcc tgc acg aga gag cag aag ccc ttc aag gcc cag       1750
Cys Arg Trp Gln Ala Cys Thr Arg Glu Gln Lys Pro Phe Lys Ala Gln
            455                 460                 465
```

```
                                                                -continued tac atg ctg gtt gtt cac atg cgc aga cac acg ggt gag aag cca cac    1798
Tyr Met Leu Val Val His Met Arg Arg His Thr Gly Glu Lys Pro His
        470                 475                 480 aag tgc acg ttc gaa ggc tgt tcc aag gcc tac tct cgc ctg gag aac    1846
Lys Cys Thr Phe Glu Gly Cys Ser Lys Ala Tyr Ser Arg Leu Glu Asn
    485                 490                 495 ctg aag aca cac ctg cgt tca cac aca gga gag aag cca tat gtg tgt    1894
Leu Lys Thr His Leu Arg Ser His Thr Gly Glu Lys Pro Tyr Val Cys
500                 505                 510                 515 gaa cac gaa ggc tgt aac aaa gcc ttc tcc aat gcc tca gac cgc gcc    1942
Glu His Glu Gly Cys Asn Lys Ala Phe Ser Asn Ala Ser Asp Arg Ala
                520                 525                 530 aag cac cag aac cgc act cac tcc aat gag aaa ccc tac atc tgc aag    1990
Lys His Gln Asn Arg Thr His Ser Asn Glu Lys Pro Tyr Ile Cys Lys
            535                 540                 545 atc cca ggc tgc acc aag agg tac aca gac ccc agc tca ctc cgc aag    2038
Ile Pro Gly Cys Thr Lys Arg Tyr Thr Asp Pro Ser Ser Leu Arg Lys
        550                 555                 560 cat gtg aag act gtc cat ggg cca gac gcc cat gtc acc aag aaa cag    2086
His Val Lys Thr Val His Gly Pro Asp Ala His Val Thr Lys Lys Gln
    565                 570                 575 cgt aat gat gtg cat gtc cgt gct cca ctg ctc aag gag aat ggg gat    2134
Arg Asn Asp Val His Val Arg Ala Pro Leu Leu Lys Glu Asn Gly Asp
580                 585                 590                 595 aat gag gcc agc gcc gag cca ggt ggc cgg gga cct gag gag agt gtg    2182
Asn Glu Ala Ser Ala Glu Pro Gly Gly Arg Gly Pro Glu Glu Ser Val
                600                 605                 610 gag gcc agt agc acc agc cac act gtg gag gac tgc cta cat atc aaa    2230
Glu Ala Ser Ser Thr Ser His Thr Val Glu Asp Cys Leu His Ile Lys
            615                 620                 625 gcc atc aag aca gag agc tcc ggg ctt tgt cag tcc agc ccc ggg gcc    2278
Ala Ile Lys Thr Glu Ser Ser Gly Leu Cys Gln Ser Ser Pro Gly Ala
        630                 635                 640 cag tca tcc tgc agc agc gag ccc tct ccc ctg ggc agt gcc ccc aac    2326
Gln Ser Ser Cys Ser Ser Glu Pro Ser Pro Leu Gly Ser Ala Pro Asn
    645                 650                 655 aat gac agt ggc atg gag atg ccg ggg aca ggg cct ggg agt ctg gga    2374
Asn Asp Ser Gly Met Glu Met Pro Gly Thr Gly Pro Gly Ser Leu Gly
660                 665                 670                 675 gac ctg aca gca ctg gct gac acg tgt cca gga gct gac acc tca gcc    2422
Asp Leu Thr Ala Leu Ala Asp Thr Cys Pro Gly Ala Asp Thr Ser Ala
                680                 685                 690 ctg gct gca ccc tcc act ggt ggc ctg cag ctg cgc aaa cac atg agc    2470
Leu Ala Ala Pro Ser Thr Gly Gly Leu Gln Leu Arg Lys His Met Ser
            695                 700                 705 acc gtg cat cgc ttt gag cag ctg aag aga gag aag ctc aag tca ctg    2518
Thr Val His Arg Phe Glu Gln Leu Lys Arg Glu Lys Leu Lys Ser Leu
        710                 715                 720 aag gat tcc tgc tcg tgg gcc ggc cca gct cca cac acc cgc aac acc    2566
Lys Asp Ser Cys Ser Trp Ala Gly Pro Ala Pro His Thr Arg Asn Thr
725                 730                 735 aag ctg cct ccc ctt cca gtc aat ggt tct gtc ctg gaa aac ttc aac    2614
Lys Leu Pro Pro Leu Pro Val Asn Gly Ser Val Leu Glu Asn Phe Asn
                740                 745                 750                 755 aat aca ggg ggt gga gga ccg gca gga ctg ctg ccc agc cag cgg cta    2662
Asn Thr Gly Gly Gly Gly Pro Ala Gly Leu Leu Pro Ser Gln Arg Leu
            760                 765                 770 cca gag ctg acc gaa gtg acg atg ctg agc cag ctg cag gaa cga aga    2710
Pro Glu Leu Thr Glu Val Thr Met Leu Ser Gln Leu Gln Glu Arg Arg
        775                 780                 785
```

-continued

| | | |
|---|---|---|
| gac agc tcc acc agc acc atg agc tcg gcc tac act gtg agc cgc cgc<br>Asp Ser Ser Thr Ser Thr Met Ser Ser Ala Tyr Thr Val Ser Arg Arg<br>790                        795                        800 | 2758 |
| tcc tct ggc atc tcc cca tac ttc tct agc cgt cgc tcc agc gag gct<br>Ser Ser Gly Ile Ser Pro Tyr Phe Ser Ser Arg Arg Ser Ser Glu Ala<br>805                        810                        815 | 2806 |
| tcg cct ctc ggt ggc cta cgc ccg cac aac gcc agc tca gca gac tcc<br>Ser Pro Leu Gly Gly Leu Arg Pro His Asn Ala Ser Ser Ala Asp Ser<br>820                        825                        830                        835 | 2854 |
| tat gac ccc atc tcc aca gat gcc tct cgg cgc tcc agt gaa gcc agc<br>Tyr Asp Pro Ile Ser Thr Asp Ala Ser Arg Arg Ser Ser Glu Ala Ser<br>                      840                        845                        850 | 2902 |
| cag tgc agt ggc ggt ggc cca ggg ctg ctc aac ctc aca cct gcg cag<br>Gln Cys Ser Gly Gly Gly Pro Gly Leu Leu Asn Leu Thr Pro Ala Gln<br>                      855                        860                        865 | 2950 |
| cag tac aac ctg cgt gcc aag tac gca gcg gcc aca ggt gga cca ccg<br>Gln Tyr Asn Leu Arg Ala Lys Tyr Ala Ala Ala Thr Gly Gly Pro Pro<br>                      870                        875                        880 | 2998 |
| ccc acg cca ctg ccg ggc ctc gat cgt gta agc ctt cgt acc cgc ctg<br>Pro Thr Pro Leu Pro Gly Leu Asp Arg Val Ser Leu Arg Thr Arg Leu<br>885                        890                        895 | 3046 |
| gcc ttg ctg gat gct cct gag cgt gca ctt cct ggt gcc tgc cca cat<br>Ala Leu Leu Asp Ala Pro Glu Arg Ala Leu Pro Gly Ala Cys Pro His<br>900                        905                        910                        915 | 3094 |
| cca ctg ggg cca cgg cgt ggc agc gat ggg cct acc tat agc cat ggt<br>Pro Leu Gly Pro Arg Arg Gly Ser Asp Gly Pro Thr Tyr Ser His Gly<br>                      920                        925                        930 | 3142 |
| cat ggc cat ggc tac gca ggt gcg gct cca gca ttc ccc cac gag ggg<br>His Gly His Gly Tyr Ala Gly Ala Ala Pro Ala Phe Pro His Glu Gly<br>                      935                        940                        945 | 3190 |
| cca aac agc agc aca cgg cgg gcc agc gac cct gtg cgg cgc cct gac<br>Pro Asn Ser Ser Thr Arg Arg Ala Ser Asp Pro Val Arg Arg Pro Asp<br>                      950                        955                        960 | 3238 |
| ccc ctt att ctg cct cga gtg caa cgt ttc cac agt acc cac aac atg<br>Pro Leu Ile Leu Pro Arg Val Gln Arg Phe His Ser Thr His Asn Met<br>965                        970                        975 | 3286 |
| aat cca ggt tca ctg cca ccc tgc gct gat cgg cgt ggc ctg cac gta<br>Asn Pro Gly Ser Leu Pro Pro Cys Ala Asp Arg Arg Gly Leu His Val<br>980                        985                        990                        995 | 3334 |
| cag agc cac ccc agc gta gac agc aac ctg acc cgc aac gcc tac<br>Gln Ser His Pro Ser Val Asp Ser Asn Leu Thr Arg Asn Ala Tyr<br>                     1000                   1005                   1010 | 3379 |
| tct ccc aga ccc cct agc atc aat gag aac gtg gtg atg gag gcc<br>Ser Pro Arg Pro Pro Ser Ile Asn Glu Asn Val Val Met Glu Ala<br>                     1015                   1020                   1025 | 3424 |
| gtg gct gct ggg gta gac ggc cca ggg cta gag tgc gac ctg ggg<br>Val Ala Ala Gly Val Asp Gly Pro Gly Leu Glu Cys Asp Leu Gly<br>                     1030                   1035                   1040 | 3469 |
| ctg gtg gag gat gag ctg gtg ctg cca gat gat gtg gta cag tac<br>Leu Val Glu Asp Glu Leu Val Leu Pro Asp Asp Val Val Gln Tyr<br>                     1045                   1050                   1055 | 3514 |
| atc aag gct cac acc ggt ggt acc ttg gat gac ggc att cgg cag<br>Ile Lys Ala His Thr Gly Gly Thr Leu Asp Asp Gly Ile Arg Gln<br>                     1060                   1065                   1070 | 3559 |
| ggg tat ccc aca gaa ggt act ggc ttc ccc gag aac tct aag ctg<br>Gly Tyr Pro Thr Glu Gly Thr Gly Phe Pro Glu Asn Ser Lys Leu<br>                     1075                   1080                   1085 | 3604 |
| ccc agt cct ggg cta caa ggc cac cgc agg cta gca gct gcc gac<br>Pro Ser Pro Gly Leu Gln Gly His Arg Arg Leu Ala Ala Ala Asp<br>                     1090                   1095                   1100 | 3649 |

| | | |
|---|---|---|
| tcc aac atg ggt cct tct gct cct gga ctc ggg ggc tgc cag ctg<br>Ser Asn Met Gly Pro Ser Ala Pro Gly Leu Gly Gly Cys Gln Leu<br>1105                     1110                    1115 | 3694 |
| agc tac agc ccc tcc tcc aac ctc aac aag agc aac atg cct gtg<br>Ser Tyr Ser Pro Ser Ser Asn Leu Asn Lys Ser Asn Met Pro Val<br>1120                     1125                    1130 | 3739 |
| cag tgg aat gag gtg agt tct ggc acc gtg gat gcc ctg cct acc<br>Gln Trp Asn Glu Val Ser Ser Gly Thr Val Asp Ala Leu Pro Thr<br>1135                     1140                    1145 | 3784 |
| cag gtg aag cca cct cct ttc cct cac agc aac ctg gct gtg gtc<br>Gln Val Lys Pro Pro Pro Phe Pro His Ser Asn Leu Ala Val Val<br>1150                     1155                    1160 | 3829 |
| caa cag aag cca gcc ttt ggc cag tat cca gga tat aat cca caa<br>Gln Gln Lys Pro Ala Phe Gly Gln Tyr Pro Gly Tyr Asn Pro Gln<br>1165                     1170                    1175 | 3874 |
| tcc gtg cag agc agc tcc gga ggt cta gac agc acc cag ccg cac<br>Ser Val Gln Ser Ser Ser Gly Gly Leu Asp Ser Thr Gln Pro His<br>1180                     1185                    1190 | 3919 |
| cta cag ctt cga gga gcc ccc tct gca tca aga ggg agc tac acg<br>Leu Gln Leu Arg Gly Ala Pro Ser Ala Ser Arg Gly Ser Tyr Thr<br>1195                     1200                    1205 | 3964 |
| caa cag cct cga cag cca gct gca ggc agt cag tgc ctg ggt atg<br>Gln Gln Pro Arg Gln Pro Ala Ala Gly Ser Gln Cys Leu Gly Met<br>1210                     1215                    1220 | 4009 |
| agt gcg gcc atg agc ccg cag gcc agc tac agc caa gcc cac ccc<br>Ser Ala Ala Met Ser Pro Gln Ala Ser Tyr Ser Gln Ala His Pro<br>1225                     1230                    1235 | 4054 |
| cag ctg agc cca aac att gtc agc gga tct ctg aac cag ttt tct<br>Gln Leu Ser Pro Asn Ile Val Ser Gly Ser Leu Asn Gln Phe Ser<br>1240                     1245                    1250 | 4099 |
| ccc tcc tgc agc aat atg gca gcc aag ccc agc cac ctg gga ctc<br>Pro Ser Cys Ser Asn Met Ala Ala Lys Pro Ser His Leu Gly Leu<br>1255                     1260                    1265 | 4144 |
| cct cag caa atg gaa gtt gtc ccc aat gcc acc atc atg aat ggc<br>Pro Gln Gln Met Glu Val Val Pro Asn Ala Thr Ile Met Asn Gly<br>1270                     1275                    1280 | 4189 |
| cat caa cgg gag cac ggg gtc ccc aat tca tcc ctg gct gcg gtg<br>His Gln Arg Glu His Gly Val Pro Asn Ser Ser Leu Ala Ala Val<br>1285                     1290                    1295 | 4234 |
| tca caa cct cac cca gtc ctg agc tat ccc cag cag gac agc tac<br>Ser Gln Pro His Pro Val Leu Ser Tyr Pro Gln Gln Asp Ser Tyr<br>1300                     1305                    1310 | 4279 |
| caa cag ggc tcc aac ctt ctg tca tcc cat cag cct ggc ttc atg<br>Gln Gln Gly Ser Asn Leu Leu Ser Ser His Gln Pro Gly Phe Met<br>1315                     1320                    1325 | 4324 |
| gag tcc cag cag aac gcg ggc ttt ggt ctc atg cag cct cgg cca<br>Glu Ser Gln Gln Asn Ala Gly Phe Gly Leu Met Gln Pro Arg Pro<br>1330                     1335                    1340 | 4369 |
| ccc ctg gaa ccc aac acg gcc agc cgt cac cgt gga gta cgt tct<br>Pro Leu Glu Pro Asn Thr Ala Ser Arg His Arg Gly Val Arg Ser<br>1345                     1350                    1355 | 4414 |
| ggg caa cag cag ttg tat gcc agg acc act ggc caa gcc atg gtc<br>Gly Gln Gln Gln Leu Tyr Ala Arg Thr Thr Gly Gln Ala Met Val<br>1360                     1365                    1370 | 4459 |
| aca tca gcc aac caa gag aca gca gaa gct atg ccc aag gga cca<br>Thr Ser Ala Asn Gln Glu Thr Ala Glu Ala Met Pro Lys Gly Pro<br>1375                     1380                    1385 | 4504 |
| gca ggg acc atg gta tcc cta gct cct cag cca tct cag gac aca<br>Ala Gly Thr Met Val Ser Leu Ala Pro Gln Pro Ser Gln Asp Thr<br>1390                     1395                    1400 | 4549 |

| | | |
|---|---|---|
| ggg cgg gca caa gat cag aac acg cta tac tac tat ggc cag atc<br>Gly Arg Ala Gln Asp Gln Asn Thr Leu Tyr Tyr Tyr Gly Gln Ile<br>    1405                1410                1415 | | 4594 |
| cac atg tat gaa cag aat gga ggc tgc cca gcc gtg cag ccc cag<br>His Met Tyr Glu Gln Asn Gly Gly Cys Pro Ala Val Gln Pro Gln<br>    1420                1425                1430 | | 4639 |
| ccg cca caa cca caa gct tgc tca gac agt atc cag cct gag cct<br>Pro Pro Gln Pro Gln Ala Cys Ser Asp Ser Ile Gln Pro Glu Pro<br>    1435                1440                1445 | | 4684 |
| ttg cct tca ccg gga gtc aac cag gtg tct agc acc gtg gac tcc<br>Leu Pro Ser Pro Gly Val Asn Gln Val Ser Ser Thr Val Asp Ser<br>    1450                1455                1460 | | 4729 |
| cag ctc ctg gag ccc ccc cag att gac ttt gat gcc atc atg gat<br>Gln Leu Leu Glu Pro Pro Gln Ile Asp Phe Asp Ala Ile Met Asp<br>    1465                1470                1475 | | 4774 |
| gat ggt gat cac tcg agt ttg ttt tct ggt gca ctg agc cca acc<br>Asp Gly Asp His Ser Ser Leu Phe Ser Gly Ala Leu Ser Pro Thr<br>    1480                1485                1490 | | 4819 |
| ctt ctc cac aat ctc tcc cag aat tcc tca cgc ctc acc aca ccc<br>Leu Leu His Asn Leu Ser Gln Asn Ser Ser Arg Leu Thr Thr Pro<br>    1495                1500                1505 | | 4864 |
| cgg aat tcc ttg aca ctg ccc tcc atc cct gcg ggc atc agc aac<br>Arg Asn Ser Leu Thr Leu Pro Ser Ile Pro Ala Gly Ile Ser Asn<br>    1510                1515                1520 | | 4909 |
| atg gcc gtg ggc gac atg agt tcc atg ctc acc agc ctg gct gaa<br>Met Ala Val Gly Asp Met Ser Ser Met Leu Thr Ser Leu Ala Glu<br>    1525                1530                1535 | | 4954 |
| gag agc aag ttt tta aac atg atg acc taaaggccct ggctcctggc<br>Glu Ser Lys Phe Leu Asn Met Met Thr<br>    1540 | | 5001 |
| acaggagacc tgagcaacac tagccccttg aatatgagg gtctagtctg ttctcattgt | | 5061 |
| cccaaagtgt taactaggcc tgagaggggt tgggcaatgg ccaactccaa atgacagctc | | 5121 |
| tgggccatgc ccagggtct tcttgcagat gtttttaagaa aagattaagg ggcatcctct | | 5181 |
| ctgctgtttg gcctatttgg gggggaggg acacccaaa gtcttattca aaagaaact | | 5241 |
| cgttcacatg acgcttgcca gcctctggtg tttgtgagat tcccgggttc tggctccttt | | 5301 |
| gcctctatca ttcagctaat gagagagaac tttggccagg ggcttttcaa gtacacgccc | | 5361 |
| aaagagggga ggggagccac tctgggtttg aatctgagac catgctggat attctctgct | | 5421 |
| ctgagaagat gagtttgcca ttctgccacc tgggaggaaa agggattact gtttcccctg | | 5481 |
| gattcttcca tgaagctcgt caaggttgct caccacggag gagaaaggcg catccccgg | | 5541 |
| gatattgtag tctcctcagt tacttgctaa catctccatt tccttaggta gagtgggacc | | 5601 |
| agcagatttc ctaaatggag aagaattaat aaaacacgta ttttactatt gggggggta | | 5661 |
| cagggtctct cctggcctgt ttacagtgtt ctgaggtata cagtgaagcc ctccctggga | | 5721 |
| agaagacttg cgtctacatg ccttgggttg ctgtggacta ggaataggca gggcctcgag | | 5781 |
| gtggaagagg ccttccccag gaaaaggaag tcatatgttt acccgctcct atttctccag | | 5841 |
| tgcactatct gaccactctc tcatgggaga tcccagggct cctccacacc ggctggtggc | | 5901 |
| cagcagacaa ccctgagcga ccacctgcag cctccacact ttctggtccc ctgacctcta | | 5961 |
| ccctcctctc caggttattt ggcatggacc agtgatgaca tgcatggttt gtggttgagc | | 6021 |
| ggaaggttga aggcattgat tcttggactt tgaggaactc ttaactgaat ttgcttgttc | | 6081 |
| agtatggcct ggccccagat aagaaatggc atgtggaaac tgactccaaa agagtcagt | | 6141 |
| cagagcgcac tgcagggtga acccatgcct ccaccaccac agacatgtgc gtatcccaaa | | 6201 |

```
cctgttcctt tgagttaaca gaaactttg ccaaccaaac ctcaccaatc agagcttcct    6261
tctggccatg accttggctg tggtgaggag cttcttaaca gagtctggac cctctgtgtc    6321
ccagggcagc aaacttctct gtttacaacc cagagacagg accaactcca aatgacagct    6381
ctgggccatg cccctgggtc tctggctctt gtggtgtgga ctcattgcct gacatagacc    6441
ctagcttccc attctgtctg tatctatttt gtgtagacat cgtcttgcct gaatagactg    6501
tgggtgaatc caaatttggt ccagccaaat ttatattgcc aaacattttt agcttttct     6561 acatgctata aattgagatg acatgctcaa cttgtaaata agtctttttt gtacattaaa    6621
agtaattttt tcataattta tcttgttgat ctgcttttcc cttgacagta gttaatgaga    6681
atccaggcag taaatttggt gcatttg                                          6708
```

<210> SEQ ID NO 2
<211> LENGTH: 1544
<212> TYPE: PRT
<213> ORGANISM: Mus musculus

<400> SEQUENCE: 2

```
Met Glu Thr Ser Ala Pro Ala Pro Ala Leu Glu Lys Lys Glu Ala Lys
1               5                   10                  15

Ser Gly Leu Leu Glu Asp Ser Ser Phe Pro Asp Pro Gly Lys Lys Ala
            20                  25                  30

Cys Pro Leu Ala Val Ala Ala Val Ala Ala His Gly Val Pro Gln
        35                  40                  45

Gln Leu Leu Pro Ala Phe His Ala Pro Leu Pro Ile Asp Met Arg His
    50                  55                  60

Gln Glu Gly Arg Tyr His Tyr Asp Pro His Ser Val His Ser Val His
65                  70                  75                  80

Gly Pro Pro Thr Leu Ser Gly Ser Pro Val Ile Ser Asp Ile Ser Leu
                85                  90                  95

Ile Arg Leu Ser Pro His Pro Ala Gly Pro Gly Glu Ser Pro Phe Ser
            100                 105                 110

Ala His His Pro Tyr Val Asn Pro His Met Glu His Tyr Leu Arg Ser
        115                 120                 125

Val His Ser Ser Pro Thr Leu Ser Met Ile Ser Ala Ala Arg Gly Leu
    130                 135                 140

Ser Pro Ala Asp Val Ala His Glu His Leu Lys Glu Arg Gly Leu Phe
145                 150                 155                 160

Ser Leu Ala Ala Pro Gly Thr Asn Pro Ser Asp Tyr Tyr His Gln Met
                165                 170                 175

Thr Leu Met Ala Ser His Pro Thr Pro Tyr Gly Asp Leu Leu Met Gln
            180                 185                 190

Ser Gly Gly Ala Ala Ser Ala Pro His Leu His Asp Tyr Leu Asn Pro
        195                 200                 205

Val Asp Ala Ser Arg Phe Ser Ser Pro Arg Val Thr Pro Arg Leu Ser
    210                 215                 220

Arg Lys Arg Ala Leu Ser Ile Ser Pro Leu Ser Asp Ala Ser Leu Asp
225                 230                 235                 240

Leu Gln Arg Met Ile Arg Thr Ser Pro Asn Ser Leu Val Ala Tyr Ile
                245                 250                 255

Asn Asn Ser Arg Ser Ser Ser Ala Ala Ser Gly Ser Tyr Gly His Leu
            260                 265                 270

Ser Ala Gly Ala Leu Ser Pro Ala Phe Thr Phe Pro His Pro Ile Asn
        275                 280                 285
```

```
Pro Val Ala Tyr Gln Gln Ile Leu Ser Gln Gln Arg Gly Leu Gly Ser
    290                 295                 300

Ala Phe Gly His Thr Pro Leu Ile Gln Pro Ser Pro Thr Phe Leu
305                 310                 315                 320

Ala Gln Gln Pro Met Thr Leu Thr Ser Ile Ser Thr Met Pro Thr Gln
                325                 330                 335

Leu Ser Ser Ser Ser Asn Cys Leu Asn Asp Ala Asn Gln Asn Lys
            340                 345                 350

Gln Asn Ser Glu Ser Ala Val Ser Ser Val Asn Pro Ile Thr Ile
                355                 360                 365

His Lys Arg Ser Lys Val Lys Thr Glu Ala Glu Gly Leu Arg Pro Ala
    370                 375                 380

Ser Pro Leu Gly Leu Thr Gln Glu Gln Leu Ala Asp Leu Lys Glu Asp
385                 390                 395                 400

Leu Asp Arg Asp Asp Cys Lys Gln Glu Ala Glu Val Val Ile Tyr Glu
                405                 410                 415

Thr Asn Cys His Trp Ala Asp Cys Thr Lys Glu Tyr Asp Thr Gln Glu
                420                 425                 430

Gln Leu Val His His Ile Asn Glu His Ile His Gly Glu Lys Lys
    435                 440                 445

Glu Phe Val Cys Arg Trp Gln Ala Cys Thr Arg Glu Gln Lys Pro Phe
    450                 455                 460

Lys Ala Gln Tyr Met Leu Val Val His Met Arg Arg His Thr Gly Glu
465                 470                 475                 480

Lys Pro His Lys Cys Thr Phe Glu Gly Cys Ser Lys Ala Tyr Ser Arg
                485                 490                 495

Leu Glu Asn Leu Lys Thr His Leu Arg Ser His Thr Gly Glu Lys Pro
            500                 505                 510

Tyr Val Cys Glu His Glu Gly Cys Asn Lys Ala Phe Ser Asn Ala Ser
                515                 520                 525

Asp Arg Ala Lys His Gln Asn Arg Thr His Ser Asn Glu Lys Pro Tyr
530                 535                 540

Ile Cys Lys Ile Pro Gly Cys Thr Lys Arg Tyr Thr Asp Pro Ser Ser
545                 550                 555                 560

Leu Arg Lys His Val Lys Thr Val His Gly Pro Asp Ala His Val Thr
                565                 570                 575

Lys Lys Gln Arg Asn Asp Val His Val Arg Ala Pro Leu Leu Lys Glu
            580                 585                 590

Asn Gly Asp Asn Glu Ala Ser Ala Glu Pro Gly Gly Arg Gly Pro Glu
            595                 600                 605

Glu Ser Val Glu Ala Ser Ser Thr Ser His Thr Val Glu Asp Cys Leu
    610                 615                 620

His Ile Lys Ala Ile Lys Thr Glu Ser Ser Gly Leu Cys Gln Ser Ser
625                 630                 635                 640

Pro Gly Ala Gln Ser Ser Cys Ser Ser Glu Pro Ser Pro Leu Gly Ser
                645                 650                 655

Ala Pro Asn Asn Asp Ser Gly Met Glu Met Pro Gly Thr Gly Pro Gly
            660                 665                 670

Ser Leu Gly Asp Leu Thr Ala Leu Ala Asp Thr Cys Pro Gly Ala Asp
            675                 680                 685

Thr Ser Ala Leu Ala Ala Pro Ser Thr Gly Gly Leu Gln Leu Arg Lys
    690                 695                 700

His Met Ser Thr Val His Arg Phe Glu Gln Leu Lys Arg Glu Lys Leu
```

-continued

```
            705                 710                 715                 720
Lys Ser Leu Lys Asp Ser Cys Ser Trp Ala Gly Pro Ala Pro His Thr
                    725                 730                 735

Arg Asn Thr Lys Leu Pro Pro Leu Pro Val Asn Gly Ser Val Leu Glu
                740                 745                 750

Asn Phe Asn Asn Thr Gly Gly Gly Pro Ala Gly Leu Leu Pro Ser
            755                 760                 765

Gln Arg Leu Pro Glu Leu Thr Glu Val Thr Met Leu Ser Gln Leu Gln
            770                 775                 780

Glu Arg Arg Asp Ser Ser Thr Ser Thr Met Ser Ser Ala Tyr Thr Val
785                 790                 795                 800

Ser Arg Arg Ser Ser Gly Ile Ser Pro Tyr Phe Ser Ser Arg Arg Ser
                805                 810                 815

Ser Glu Ala Ser Pro Leu Gly Gly Leu Arg Pro His Asn Ala Ser Ser
                820                 825                 830

Ala Asp Ser Tyr Asp Pro Ile Ser Thr Asp Ala Ser Arg Arg Ser Ser
            835                 840                 845

Glu Ala Ser Gln Cys Ser Gly Gly Pro Gly Leu Leu Asn Leu Thr
850                 855                 860

Pro Ala Gln Gln Tyr Asn Leu Arg Ala Lys Tyr Ala Ala Thr Gly
865                 870                 875                 880

Gly Pro Pro Pro Thr Pro Leu Pro Gly Leu Asp Arg Val Ser Leu Arg
                885                 890                 895

Thr Arg Leu Ala Leu Leu Asp Ala Pro Glu Arg Ala Leu Pro Gly Ala
                900                 905                 910

Cys Pro His Pro Leu Gly Pro Arg Arg Gly Ser Asp Gly Pro Thr Tyr
            915                 920                 925

Ser His Gly His Gly His Gly Tyr Ala Gly Ala Ala Pro Ala Phe Pro
            930                 935                 940

His Glu Gly Pro Asn Ser Ser Thr Arg Arg Ala Ser Asp Pro Val Arg
945                 950                 955                 960

Arg Pro Asp Pro Leu Ile Leu Pro Arg Val Gln Arg Phe His Ser Thr
                965                 970                 975

His Asn Met Asn Pro Gly Ser Leu Pro Pro Cys Ala Asp Arg Arg Gly
            980                 985                 990

Leu His Val Gln Ser His Pro Ser  Val Asp Ser Asn Leu  Thr Arg Asn
                995                  1000                 1005

Ala Tyr  Ser Pro Arg Pro  Ser Ile Asn Glu Asn  Val Val Met
    1010                 1015                 1020

Glu Ala  Val Ala Ala Gly Val  Asp Gly Pro Gly Leu  Glu Cys Asp
     1025                 1030                 1035

Leu Gly  Leu Val Glu Asp Glu  Leu Val Leu Pro Asp  Asp Val Val
     1040                 1045                 1050

Gln Tyr  Ile Lys Ala His Thr  Gly Gly Thr Leu Asp  Asp Gly Ile
     1055                 1060                 1065

Arg Gln  Gly Tyr Pro Thr Glu  Gly Thr Gly Phe Pro  Glu Asn Ser
     1070                 1075                 1080

Lys Leu  Pro Ser Pro Gly Leu  Gln Gly His Arg Arg  Leu Ala Ala
     1085                 1090                 1095

Ala Asp  Ser Asn Met Gly Pro  Ser Ala Pro Gly Leu  Gly Gly Cys
     1100                 1105                 1110

Gln Leu  Ser Tyr Ser Pro Ser  Ser Asn Leu Asn Lys  Ser Asn Met
     1115                 1120                 1125
```

-continued

```
Pro Val Gln Trp Asn Glu Val Ser Ser Gly Thr Val Asp Ala Leu
    1130                1135                1140

Pro Thr Gln Val Lys Pro Pro Phe Pro His Ser Asn Leu Ala
    1145                1150                1155

Val Val Gln Gln Lys Pro Ala Phe Gly Gln Tyr Pro Gly Tyr Asn
    1160                1165                1170

Pro Gln Ser Val Gln Ser Ser Gly Gly Leu Asp Ser Thr Gln
    1175                1180                1185

Pro His Leu Gln Leu Arg Gly Ala Pro Ser Ala Ser Arg Gly Ser
    1190                1195                1200

Tyr Thr Gln Gln Pro Arg Gln Pro Ala Ala Gly Ser Gln Cys Leu
    1205                1210                1215

Gly Met Ser Ala Ala Met Ser Pro Gln Ala Ser Tyr Ser Gln Ala
    1220                1225                1230

His Pro Gln Leu Ser Pro Asn Ile Val Ser Gly Ser Leu Asn Gln
    1235                1240                1245

Phe Ser Pro Ser Cys Ser Asn Met Ala Ala Lys Pro Ser His Leu
    1250                1255                1260

Gly Leu Pro Gln Gln Met Glu Val Val Pro Asn Ala Thr Ile Met
    1265                1270                1275

Asn Gly His Gln Arg Glu His Gly Val Pro Asn Ser Ser Leu Ala
    1280                1285                1290

Ala Val Ser Gln Pro His Pro Val Leu Ser Tyr Pro Gln Gln Asp
    1295                1300                1305

Ser Tyr Gln Gln Gly Ser Asn Leu Leu Ser Ser His Gln Pro Gly
    1310                1315                1320

Phe Met Glu Ser Gln Gln Asn Ala Gly Phe Gly Leu Met Gln Pro
    1325                1330                1335

Arg Pro Pro Leu Glu Pro Asn Thr Ala Ser Arg His Arg Gly Val
    1340                1345                1350

Arg Ser Gly Gln Gln Gln Leu Tyr Ala Arg Thr Thr Gly Gln Ala
    1355                1360                1365

Met Val Thr Ser Ala Asn Gln Glu Thr Ala Glu Ala Met Pro Lys
    1370                1375                1380

Gly Pro Ala Gly Thr Met Val Ser Leu Ala Pro Gln Pro Ser Gln
    1385                1390                1395

Asp Thr Gly Arg Ala Gln Asp Gln Asn Thr Leu Tyr Tyr Tyr Gly
    1400                1405                1410

Gln Ile His Met Tyr Glu Gln Asn Gly Gly Cys Pro Ala Val Gln
    1415                1420                1425

Pro Gln Pro Pro Gln Pro Gln Ala Cys Ser Asp Ser Ile Gln Pro
    1430                1435                1440

Glu Pro Leu Pro Ser Pro Gly Val Asn Gln Val Ser Ser Thr Val
    1445                1450                1455

Asp Ser Gln Leu Leu Glu Pro Pro Gln Ile Asp Phe Asp Ala Ile
    1460                1465                1470

Met Asp Asp Gly Asp His Ser Ser Leu Phe Ser Gly Ala Leu Ser
    1475                1480                1485

Pro Thr Leu Leu His Asn Leu Ser Gln Asn Ser Ser Arg Leu Thr
    1490                1495                1500

Thr Pro Arg Asn Ser Leu Thr Leu Pro Ser Ile Pro Ala Gly Ile
    1505                1510                1515

Ser Asn Met Ala Val Gly Asp Met Ser Ser Met Leu Thr Ser Leu
    1520                1525                1530
```

```
Ala Glu  Glu Ser Lys Phe Leu  Asn Met Met Thr
    1535            1540

<210> SEQ ID NO 3
<211> LENGTH: 33
<212> TYPE: DNA
<213> ORGANISM: Artificial Sequence
<220> FEATURE:
<223> OTHER INFORMATION: PCR Primer mutagenesis

<400> SEQUENCE: 3
gcccccaaca atgacgccgg catggagatg ccg                                33

<210> SEQ ID NO 4
<211> LENGTH: 33
<212> TYPE: DNA
<213> ORGANISM: Artificial Sequence
<220> FEATURE:
<223> OTHER INFORMATION: PCR Primer for Mutagenesis

<400> SEQUENCE: 4
cggcatctcc atgccggcgt cattgttggg ggc                                33

<210> SEQ ID NO 5
<211> LENGTH: 4634
<212> TYPE: DNA
<213> ORGANISM: Artificial Sequence
<220> FEATURE:
<223> OTHER INFORMATION: Mutated Gli2 sequence
<220> FEATURE:
<221> NAME/KEY: CDS
<222> LOCATION: (1)..(4632)

<400> SEQUENCE: 5
```

| | | | | | | | | | | | | | | | | |
|---|---|---|---|---|---|---|---|---|---|---|---|---|---|---|---|---|
| atg | gag | act | tct | gcc | cca | gcc | cct | gca | ctg | gag | aag | aaa | gaa | gcc | aag | 48 |
| Met | Glu | Thr | Ser | Ala | Pro | Ala | Pro | Ala | Leu | Glu | Lys | Lys | Glu | Ala | Lys | |
| 1 | | | 5 | | | | | 10 | | | | | 15 | | | |
| agt | ggt | ctc | ttg | gag | gac | agc | agc | ttc | ccc | gac | cca | ggg | aaa | aag | gcc | 96 |
| Ser | Gly | Leu | Leu | Glu | Asp | Ser | Ser | Phe | Pro | Asp | Pro | Gly | Lys | Lys | Ala | |
| | | | 20 | | | | | 25 | | | | 30 | | | | |
| tgt | cct | ctg | gcg | gtg | gcc | gca | gct | gta | gcc | gcc | cac | gga | gtt | cct | cag | 144 |
| Cys | Pro | Leu | Ala | Val | Ala | Ala | Ala | Val | Ala | Ala | His | Gly | Val | Pro | Gln | |
| | | 35 | | | | | 40 | | | | | 45 | | | | |
| cag | ctc | ctg | ccg | gct | ttc | cac | gcg | cct | ttg | ccg | att | gac | atg | aga | cac | 192 |
| Gln | Leu | Leu | Pro | Ala | Phe | His | Ala | Pro | Leu | Pro | Ile | Asp | Met | Arg | His | |
| | 50 | | | | | 55 | | | | | 60 | | | | | |
| cag | gag | gga | agg | tac | cat | tat | gac | cct | cac | tct | gtc | cac | agt | gta | cac | 240 |
| Gln | Glu | Gly | Arg | Tyr | His | Tyr | Asp | Pro | His | Ser | Val | His | Ser | Val | His | |
| 65 | | | | 70 | | | | | 75 | | | | | 80 | | |
| ggg | cct | ccc | acc | cta | agt | ggc | agc | cct | gtc | atc | tca | gat | atc | tcc | ttg | 288 |
| Gly | Pro | Pro | Thr | Leu | Ser | Gly | Ser | Pro | Val | Ile | Ser | Asp | Ile | Ser | Leu | |
| | | | 85 | | | | | 90 | | | | | 95 | | | |
| ata | cga | ctt | tct | cca | cac | cct | gct | ggc | cct | gga | gag | tca | ccc | ttc | agc | 336 |
| Ile | Arg | Leu | Ser | Pro | His | Pro | Ala | Gly | Pro | Gly | Glu | Ser | Pro | Phe | Ser | |
| | | | 100 | | | | | 105 | | | | | 110 | | | |
| gcc | cac | cac | ccc | tac | gtg | aac | ccc | cat | atg | gag | cac | tac | ctc | cgg | tct | 384 |
| Ala | His | His | Pro | Tyr | Val | Asn | Pro | His | Met | Glu | His | Tyr | Leu | Arg | Ser | |
| | | 115 | | | | | 120 | | | | | 125 | | | | |
| gtg | cac | agc | agc | ccc | aca | ctc | tca | atg | atc | tct | gcc | gcc | agg | ggc | ctc | 432 |
| Val | His | Ser | Ser | Pro | Thr | Leu | Ser | Met | Ile | Ser | Ala | Ala | Arg | Gly | Leu | |
| | 130 | | | | | 135 | | | | | 140 | | | | | |
| agc | cct | gct | gat | gtg | gcc | cac | gaa | cat | ctg | aaa | gag | agg | gga | ctc | ttt | 480 |
| Ser | Pro | Ala | Asp | Val | Ala | His | Glu | His | Leu | Lys | Glu | Arg | Gly | Leu | Phe | |
| 145 | | | | 150 | | | | | 155 | | | | | 160 | | |

```
agc ctc gca gcc cca ggc acc aac cct tca gac tat tac cac cag atg      528
Ser Leu Ala Ala Pro Gly Thr Asn Pro Ser Asp Tyr Tyr His Gln Met
            165                 170                 175 acc ctc atg gca agc cac ccc acc cct tat ggg gac ctt cta atg cag      576
Thr Leu Met Ala Ser His Pro Thr Pro Tyr Gly Asp Leu Leu Met Gln
            180                 185                 190 agc ggg ggt gct gct agc gca ccc cat ctc cat gac tac ctc aac cct      624
Ser Gly Gly Ala Ala Ser Ala Pro His Leu His Asp Tyr Leu Asn Pro
            195                 200                 205 gtg gat gca tca cga ttc tct agt cca cgt gtg acc cca cga ctg agc      672
Val Asp Ala Ser Arg Phe Ser Ser Pro Arg Val Thr Pro Arg Leu Ser
    210                 215                 220 cgc aag cgg gct ctg tcc atc tcc ccg ctc tca gat gcc agc ctc gac      720
Arg Lys Arg Ala Leu Ser Ile Ser Pro Leu Ser Asp Ala Ser Leu Asp
225                 230                 235                 240 cta caa cgc atg att cgg acc tct ccc aac tcg ctg gta gct tac atc      768
Leu Gln Arg Met Ile Arg Thr Ser Pro Asn Ser Leu Val Ala Tyr Ile
            245                 250                 255 aac aac tcc agg agc agc tca gca gcc agt ggc tct tat gga cat ctg      816
Asn Asn Ser Arg Ser Ser Ser Ala Ala Ser Gly Ser Tyr Gly His Leu
            260                 265                 270 tct gct ggt gcc ctc agc cca gcc ttc act ttt ccc cac ccc atc aat      864
Ser Ala Gly Ala Leu Ser Pro Ala Phe Thr Phe Pro His Pro Ile Asn
            275                 280                 285 cct gtg gcc tac cag cag atc ctg agc cag cag cgg ggc ctg ggc tca      912
Pro Val Ala Tyr Gln Gln Ile Leu Ser Gln Gln Arg Gly Leu Gly Ser
            290                 295                 300 gcc ttt gga cac aca cca ccc ctg atc cag cct tca ccc acc ttc ttg      960
Ala Phe Gly His Thr Pro Pro Leu Ile Gln Pro Ser Pro Thr Phe Leu
305                 310                 315                 320 gcc cag cag ccc atg act ctc acc tcc atc agc acc atg cct acc caa     1008
Ala Gln Gln Pro Met Thr Leu Thr Ser Ile Ser Thr Met Pro Thr Gln
            325                 330                 335 ctc agc agc agt agc agc aac tgt cta aat gat gcc aac cag aac aag     1056
Leu Ser Ser Ser Ser Ser Asn Cys Leu Asn Asp Ala Asn Gln Asn Lys
            340                 345                 350 cag aac agc gag tca gct gtg agc agc acc gtg aac ccc atc acc att     1104
Gln Asn Ser Glu Ser Ala Val Ser Ser Thr Val Asn Pro Ile Thr Ile
            355                 360                 365 cat aag cgg agc aag gtc aag act gag gct gag ggc ctg cgt cca gca     1152
His Lys Arg Ser Lys Val Lys Thr Glu Ala Glu Gly Leu Arg Pro Ala
            370                 375                 380 tcc ccg ctt gga ctg aca cag gag cag ctg gcc gat ctc aag gaa gac     1200
Ser Pro Leu Gly Leu Thr Gln Glu Gln Leu Ala Asp Leu Lys Glu Asp
385                 390                 395                 400 ctg gac agg gat gac tgt aag cag gag gcc gag gtg gtc atc tac gag     1248
Leu Asp Arg Asp Asp Cys Lys Gln Glu Ala Glu Val Val Ile Tyr Glu
            405                 410                 415 acc aac tgc cac tgg gca gac tgc acc aag gag tat gac aca cag gag     1296
Thr Asn Cys His Trp Ala Asp Cys Thr Lys Glu Tyr Asp Thr Gln Glu
            420                 425                 430 cag ctg gtg cat cat atc aac aat gaa cac atc cac ggg gag aag aag     1344
Gln Leu Val His His Ile Asn Asn Glu His Ile His Gly Glu Lys Lys
            435                 440                 445 gag ttc gtg tgc cgc tgg cag gcc tgc acg aga gag cag aag ccc ttc     1392
Glu Phe Val Cys Arg Trp Gln Ala Cys Thr Arg Glu Gln Lys Pro Phe
            450                 455                 460 aag gcc cag tac atg ctg gtt gtt cac atg cgc aga cac acg ggt gag     1440
Lys Ala Gln Tyr Met Leu Val Val His Met Arg Arg His Thr Gly Glu
465                 470                 475                 480
```

```
aag cca cac aag tgc acg ttc gaa ggc tgt tcc aag gcc tac tct cgc     1488
Lys Pro His Lys Cys Thr Phe Glu Gly Cys Ser Lys Ala Tyr Ser Arg
            485                 490                 495 ctg gag aac ctg aag aca cac ctg cgt tca cac aca gga gag aag cca     1536
Leu Glu Asn Leu Lys Thr His Leu Arg Ser His Thr Gly Glu Lys Pro
        500                 505                 510 tat gtg tgt gaa cac gaa ggc tgt aac aaa gcc ttc tcc aat gcc tca     1584
Tyr Val Cys Glu His Glu Gly Cys Asn Lys Ala Phe Ser Asn Ala Ser
            515                 520                 525 gac cgc gcc aag cac cag aac cgc act cac tcc aat gag aaa ccc tac     1632
Asp Arg Ala Lys His Gln Asn Arg Thr His Ser Asn Glu Lys Pro Tyr
        530                 535                 540 atc tgc aag atc cca ggc tgc acc aag agg tac aca gac ccc agc tca     1680
Ile Cys Lys Ile Pro Gly Cys Thr Lys Arg Tyr Thr Asp Pro Ser Ser
545                 550                 555                 560 ctc cgc aag cat gtg aag act gtc cat ggg cca gac gcc cat gtc acc     1728
Leu Arg Lys His Val Lys Thr Val His Gly Pro Asp Ala His Val Thr
            565                 570                 575 aag aaa cag cgt aat gat gtg cat gtc cgt gct cca ctg ctc aag gag     1776
Lys Lys Gln Arg Asn Asp Val His Val Arg Ala Pro Leu Leu Lys Glu
        580                 585                 590 aat ggg gat aat gag gcc agc gcc gag cca ggt ggc cgg gga cct gag     1824
Asn Gly Asp Asn Glu Ala Ser Ala Glu Pro Gly Gly Arg Gly Pro Glu
            595                 600                 605 gag agt gtg gag gcc agt agc acc agc cac act gtg gag gac tgc cta     1872
Glu Ser Val Glu Ala Ser Ser Thr Ser His Thr Val Glu Asp Cys Leu
        610                 615                 620 cat atc aaa gcc atc aag aca gag agc tcc ggg ctt tgt cag tcc agc     1920
His Ile Lys Ala Ile Lys Thr Glu Ser Ser Gly Leu Cys Gln Ser Ser
625                 630                 635                 640 ccc ggg gcc cag tca tcc tgc agc agc gag ccc tct ccc ctg ggc agt     1968
Pro Gly Ala Gln Ser Ser Cys Ser Ser Glu Pro Ser Pro Leu Gly Ser
            645                 650                 655 gcc ccc aac aat gac gcc ggc atg gag atg ccg ggg aca ggg cct ggg     2016
Ala Pro Asn Asn Asp Ala Gly Met Glu Met Pro Gly Thr Gly Pro Gly
        660                 665                 670 agt ctg gga gac ctg aca gca ctg gct gac acg tgt cca gga gct gac     2064
Ser Leu Gly Asp Leu Thr Ala Leu Ala Asp Thr Cys Pro Gly Ala Asp
            675                 680                 685 acc tca gcc ctg gct gca ccc tcc act ggt ggc ctg cag ctg cgc aaa     2112
Thr Ser Ala Leu Ala Ala Pro Ser Thr Gly Gly Leu Gln Leu Arg Lys
        690                 695                 700 cac atg agc acc gtg cat cgc ttt gag cag ctg aag aga gag aag ctc     2160
His Met Ser Thr Val His Arg Phe Glu Gln Leu Lys Arg Glu Lys Leu
705                 710                 715                 720 aag tca ctg aag gat tcc tgc tcg tgg gcc ggc cca gct cca cac acc     2208
Lys Ser Leu Lys Asp Ser Cys Ser Trp Ala Gly Pro Ala Pro His Thr
            725                 730                 735 cgc aac acc aag ctg cct ccc ctt cca gtc aat ggt tct gtc ctg gaa     2256
Arg Asn Thr Lys Leu Pro Pro Leu Pro Val Asn Gly Ser Val Leu Glu
        740                 745                 750 aac ttc aac aat aca ggg ggc ggt gga ccg gca gga ctg ctg ccc agc     2304
Asn Phe Asn Asn Thr Gly Gly Gly Gly Pro Ala Gly Leu Leu Pro Ser
            755                 760                 765 cag cgg cta cca gag ctg acc gaa gtg acg atg ctg agc cag ctg cag     2352
Gln Arg Leu Pro Glu Leu Thr Glu Val Thr Met Leu Ser Gln Leu Gln
        770                 775                 780 gaa cga aga gac agc tcc acc agc acc atg agc tcg gcc tac act gtg     2400
Glu Arg Arg Asp Ser Ser Thr Ser Thr Met Ser Ser Ala Tyr Thr Val
785                 790                 795                 800
```

| | | |
|---|---|---|
| agc cgc cgc tcc tct ggc atc tcc cca tac ttc tct agc cgt cgc tcc<br>Ser Arg Arg Ser Ser Gly Ile Ser Pro Tyr Phe Ser Ser Arg Arg Ser<br>805 810 815 | 2448 | |
| agc gag gct tcg cct ctc ggt ggc cta cgc ccg cac aac gcc agc tca<br>Ser Glu Ala Ser Pro Leu Gly Gly Leu Arg Pro His Asn Ala Ser Ser<br>820 825 830 | 2496 | |
| gca gac tcc tat gac ccc atc tcc aca gat gcc tct cgg cgc tcc agt<br>Ala Asp Ser Tyr Asp Pro Ile Ser Thr Asp Ala Ser Arg Arg Ser Ser<br>835 840 845 | 2544 | |
| gaa gcc agc cag tgc agt ggc ggt ggc cca ggg ctg ctc aac ctc aca<br>Glu Ala Ser Gln Cys Ser Gly Gly Gly Pro Gly Leu Leu Asn Leu Thr<br>850 855 860 | 2592 | |
| cct gcg cag cag tac aac ctg cgt gcc aag tac gca gcg gcc aca ggt<br>Pro Ala Gln Gln Tyr Asn Leu Arg Ala Lys Tyr Ala Ala Ala Thr Gly<br>865 870 875 880 | 2640 | |
| gga cca ccg ccc acg cca ctg ccg ggc ctc gat cgt gta agc ctt cgt<br>Gly Pro Pro Pro Thr Pro Leu Pro Gly Leu Asp Arg Val Ser Leu Arg<br>885 890 895 | 2688 | |
| acc cgc ctg gcc ttg ctg gat gct cct gag cgt gca ctt cct ggt gcc<br>Thr Arg Leu Ala Leu Leu Asp Ala Pro Glu Arg Ala Leu Pro Gly Ala<br>900 905 910 | 2736 | |
| tgc cca cat cca ctg ggg cca cgg cgt ggc agc gat ggg cct acc tat<br>Cys Pro His Pro Leu Gly Pro Arg Arg Gly Ser Asp Gly Pro Thr Tyr<br>915 920 925 | 2784 | |
| agc cat ggt cat ggc cat ggc tac gca ggt gcg gct cca gca ttc ccc<br>Ser His Gly His Gly His Gly Tyr Ala Gly Ala Ala Pro Ala Phe Pro<br>930 935 940 | 2832 | |
| cac gag ggg cca aac agc agc aca cgg cgg gcc agc gac cct gtg cgg<br>His Glu Gly Pro Asn Ser Ser Thr Arg Arg Ala Ser Asp Pro Val Arg<br>945 950 955 960 | 2880 | |
| cgc cct gac ccc ctt att ctg cct cga gtg caa cgt ttc cac agt acc<br>Arg Pro Asp Pro Leu Ile Leu Pro Arg Val Gln Arg Phe His Ser Thr<br>965 970 975 | 2928 | |
| cac aac atg aat cca ggt tca ctg cca ccc tgc gct gat cgg cgt ggc<br>His Asn Met Asn Pro Gly Ser Leu Pro Pro Cys Ala Asp Arg Arg Gly<br>980 985 990 | 2976 | |
| ctg cac gta cag agc cac ccc agc gta gac agc aac ctg acc cgc aac<br>Leu His Val Gln Ser His Pro Ser Val Asp Ser Asn Leu Thr Arg Asn<br>995 1000 1005 | 3024 | |
| gcc tac tct ccc aga ccc cct agc atc aat gag aac gtg gtg atg<br>Ala Tyr Ser Pro Arg Pro Pro Ser Ile Asn Glu Asn Val Val Met<br>1010 1015 1020 | 3069 | |
| gag gcc gtg gct gct ggg gta gac ggc cca ggg cta gag tgc gac<br>Glu Ala Val Ala Ala Gly Val Asp Gly Pro Gly Leu Glu Cys Asp<br>1025 1030 1035 | 3114 | |
| ctg ggg ctg gtg gag gat gag ctg gtg ctg cca gat gat gtg gta<br>Leu Gly Leu Val Glu Asp Glu Leu Val Leu Pro Asp Asp Val Val<br>1040 1045 1050 | 3159 | |
| cag tac atc aag gct cac acc ggt ggt acc ttg gat gac ggc att<br>Gln Tyr Ile Lys Ala His Thr Gly Gly Thr Leu Asp Asp Gly Ile<br>1055 1060 1065 | 3204 | |
| cgg cag ggg tat ccc aca gaa ggt act ggc ttc ccc gag aac tct<br>Arg Gln Gly Tyr Pro Thr Glu Gly Thr Gly Phe Pro Glu Asn Ser<br>1070 1075 1080 | 3249 | |
| aag ctg ccc agt cct ggg cta caa ggc cac cgc agg cta gca gct<br>Lys Leu Pro Ser Pro Gly Leu Gln Gly His Arg Arg Leu Ala Ala<br>1085 1090 1095 | 3294 | |
| gcc gac tcc aac atg ggt cct tct gct cct gga ctc ggg ggc tgc<br>Ala Asp Ser Asn Met Gly Pro Ser Ala Pro Gly Leu Gly Gly Cys<br>1100 1105 1110 | 3339 | |

```
cag ctg agc tac agc ccc tcc tcc aac ctc aac aag agc aac atg      3384
Gln Leu Ser Tyr Ser Pro Ser Ser Asn Leu Asn Lys Ser Asn Met
    1115            1120                1125 cct gtg cag tgg aat gag gtg agt tct ggc acc gtg gat gcc ctg      3429
Pro Val Gln Trp Asn Glu Val Ser Ser Gly Thr Val Asp Ala Leu
    1130            1135                1140 cct acc cag gtg aag cca cct cct ttc cct cac agc aac ctg gct      3474
Pro Thr Gln Val Lys Pro Pro Pro Phe Pro His Ser Asn Leu Ala
    1145            1150                1155 gtg gtc caa cag aag cca gcc ttt ggc cag tat cca gga tat aat      3519
Val Val Gln Gln Lys Pro Ala Phe Gly Gln Tyr Pro Gly Tyr Asn
    1160            1165                1170 cca caa tcc gtg cag agc agc tcc gga ggt cta gac agc acc cag      3564
Pro Gln Ser Val Gln Ser Ser Gly Gly Leu Asp Ser Thr Gln
    1175            1180                1185 ccg cac cta cag ctt cga gga gcc ccc tct gca tca aga ggg agc      3609
Pro His Leu Gln Leu Arg Gly Ala Pro Ser Ala Ser Arg Gly Ser
    1190            1195                1200 tac acg caa cag cct cga cag cca gct gca ggc agt cag tgc ctg      3654
Tyr Thr Gln Gln Pro Arg Gln Pro Ala Ala Gly Ser Gln Cys Leu
    1205            1210                1215 ggt atg agt gcg gcc atg agc ccg cag gcc agc tac agc caa gcc      3699
Gly Met Ser Ala Ala Met Ser Pro Gln Ala Ser Tyr Ser Gln Ala
    1220            1225                1230 cac ccc cag ctg agc cca aac att gtc agc gga tct ctg aac cag      3744
His Pro Gln Leu Ser Pro Asn Ile Val Ser Gly Ser Leu Asn Gln
    1235            1240                1245 ttt tct ccc tcc tgc agc aat atg gca gcc aag ccc agc cac ctg      3789
Phe Ser Pro Ser Cys Ser Asn Met Ala Ala Lys Pro Ser His Leu
    1250            1255                1260 gga ctc cct cag caa atg gaa gtt gtc ccc aat gcc acc atc atg      3834
Gly Leu Pro Gln Gln Met Glu Val Val Pro Asn Ala Thr Ile Met
    1265            1270                1275 aat ggc cat caa cgg gag cac ggg gtc ccc aat tca tcc ctg gct      3879
Asn Gly His Gln Arg Glu His Gly Val Pro Asn Ser Ser Leu Ala
    1280            1285                1290 gcg gtg tca caa cct cac cca gtc ctg agc tat ccc cag cag gac      3924
Ala Val Ser Gln Pro His Pro Val Leu Ser Tyr Pro Gln Gln Asp
    1295            1300                1305 agc tac caa cag ggc tcc aac ctt ctg tca tcc cat cag cct ggc      3969
Ser Tyr Gln Gln Gly Ser Asn Leu Leu Ser Ser His Gln Pro Gly
    1310            1315                1320 ttc atg gag tcc cag cag aac gcg ggc ttt ggt ctc atg cag cct      4014
Phe Met Glu Ser Gln Gln Asn Ala Gly Phe Gly Leu Met Gln Pro
    1325            1330                1335 cgg cca ccc ctg gaa ccc aac acg gcc agc cgt cac cgt gga gta      4059
Arg Pro Pro Leu Glu Pro Asn Thr Ala Ser Arg His Arg Gly Val
    1340            1345                1350 cgt tct ggg caa cag cag ttg tat gcc agg acc act ggc caa gcc      4104
Arg Ser Gly Gln Gln Gln Leu Tyr Ala Arg Thr Thr Gly Gln Ala
    1355            1360                1365 atg gtc aca tca gcc aac caa gag aca gca gaa gct atg ccc aag      4149
Met Val Thr Ser Ala Asn Gln Glu Thr Ala Glu Ala Met Pro Lys
    1370            1375                1380 gga cca gca ggg acc atg gta tcc cta gct cct cag cca tct cag      4194
Gly Pro Ala Gly Thr Met Val Ser Leu Ala Pro Gln Pro Ser Gln
    1385            1390                1395 gac aca ggg cgg gca caa gat cag aac acg cta tac tac tat ggc      4239
Asp Thr Gly Arg Ala Gln Asp Gln Asn Thr Leu Tyr Tyr Tyr Gly
    1400            1405                1410
```

```
cag atc cac atg tat gaa cag aat gga ggc tgc cca gcc gtg cag       4284
Gln Ile His Met Tyr Glu Gln Asn Gly Gly Cys Pro Ala Val Gln
    1415                1420                1425 ccc cag ccg cca caa cca caa gct tgc tca gac agt atc cag cct       4329
Pro Gln Pro Pro Gln Pro Gln Ala Cys Ser Asp Ser Ile Gln Pro
1430                1435                1440 gag cct ttg cct tca ccg gga gtc aac cag gtg tct agc acc gtg       4374
Glu Pro Leu Pro Ser Pro Gly Val Asn Gln Val Ser Ser Thr Val
    1445                1450                1455 gac tcc cag ctc ctg gag ccc ccc cag att gac ttt gat gcc atc       4419
Asp Ser Gln Leu Leu Glu Pro Pro Gln Ile Asp Phe Asp Ala Ile
    1460                1465                1470 atg gat gat ggt gat cac tcg agt ttg ttt tct ggt gca ctg agc       4464
Met Asp Asp Gly Asp His Ser Ser Leu Phe Ser Gly Ala Leu Ser
1475                1480                1485 cca acc ctt ctc cac aat ctc tcc cag aat tcc tca cgc ctc acc       4509
Pro Thr Leu Leu His Asn Leu Ser Gln Asn Ser Ser Arg Leu Thr
    1490                1495                1500 aca ccc cgg aat tcc ttg aca ctg ccc tcc atc cct gcg ggc atc       4554
Thr Pro Arg Asn Ser Leu Thr Leu Pro Ser Ile Pro Ala Gly Ile
    1505                1510                1515 agc aac atg gcc gtg ggc gac atg agt tcc atg ctc acc agc ctg       4599
Ser Asn Met Ala Val Gly Asp Met Ser Ser Met Leu Thr Ser Leu
1520                1525                1530 gct gaa gag agc aag ttt tta aac atg atg acc ta                    4634
Ala Glu Glu Ser Lys Phe Leu Asn Met Met Thr
    1535                1540

<210> SEQ ID NO 6
<211> LENGTH: 1544
<212> TYPE: PRT
<213> ORGANISM: Artificial Sequence
<220> FEATURE:
<223> OTHER INFORMATION: Synthetic Construct

<400> SEQUENCE: 6

Met Glu Thr Ser Ala Pro Ala Pro Ala Leu Glu Lys Lys Glu Ala Lys
1               5                   10                  15

Ser Gly Leu Leu Glu Asp Ser Ser Phe Pro Asp Pro Gly Lys Lys Ala
                20                  25                  30

Cys Pro Leu Ala Val Ala Ala Val Ala Ala His Gly Val Pro Gln
            35                  40                  45

Gln Leu Leu Pro Ala Phe His Ala Pro Leu Pro Ile Asp Met Arg His
    50                  55                  60

Gln Glu Gly Arg Tyr His Tyr Asp Pro His Ser Val His Ser Val His
65                  70                  75                  80

Gly Pro Pro Thr Leu Ser Gly Ser Pro Val Ile Ser Asp Ile Ser Leu
                85                  90                  95

Ile Arg Leu Ser Pro His Pro Ala Gly Pro Gly Glu Ser Pro Phe Ser
            100                 105                 110

Ala His His Pro Tyr Val Asn Pro His Met Glu His Tyr Leu Arg Ser
        115                 120                 125

Val His Ser Ser Pro Thr Leu Ser Met Ile Ser Ala Ala Arg Gly Leu
    130                 135                 140

Ser Pro Ala Asp Val Ala His Glu His Leu Lys Glu Arg Gly Leu Phe
145                 150                 155                 160

Ser Leu Ala Ala Pro Gly Thr Asn Pro Ser Asp Tyr Tyr His Gln Met
                165                 170                 175
```

```
Thr Leu Met Ala Ser His Pro Thr Pro Tyr Gly Asp Leu Leu Met Gln
            180                 185                 190

Ser Gly Gly Ala Ala Ser Ala Pro His Leu His Asp Tyr Leu Asn Pro
        195                 200                 205

Val Asp Ala Ser Arg Phe Ser Ser Pro Arg Val Thr Pro Arg Leu Ser
210                 215                 220

Arg Lys Arg Ala Leu Ser Ile Ser Pro Leu Ser Asp Ala Ser Leu Asp
225                 230                 235                 240

Leu Gln Arg Met Ile Arg Thr Ser Pro Asn Ser Leu Val Ala Tyr Ile
                245                 250                 255

Asn Asn Ser Arg Ser Ser Ala Ala Ser Gly Ser Tyr Gly His Leu
            260                 265                 270

Ser Ala Gly Ala Leu Ser Pro Ala Phe Thr Phe Pro His Pro Ile Asn
        275                 280                 285

Pro Val Ala Tyr Gln Gln Ile Leu Ser Gln Gln Arg Gly Leu Gly Ser
    290                 295                 300

Ala Phe Gly His Thr Pro Pro Leu Ile Gln Pro Ser Pro Thr Phe Leu
305                 310                 315                 320

Ala Gln Gln Pro Met Thr Leu Thr Ser Ile Ser Thr Met Pro Thr Gln
                325                 330                 335

Leu Ser Ser Ser Ser Asn Cys Leu Asn Asp Ala Asn Gln Asn Lys
            340                 345                 350

Gln Asn Ser Glu Ser Ala Val Ser Ser Thr Val Asn Pro Ile Thr Ile
        355                 360                 365

His Lys Arg Ser Lys Val Lys Thr Glu Ala Glu Gly Leu Arg Pro Ala
    370                 375                 380

Ser Pro Leu Gly Leu Thr Gln Glu Gln Leu Ala Asp Leu Lys Glu Asp
385                 390                 395                 400

Leu Asp Arg Asp Asp Cys Lys Gln Glu Ala Glu Val Val Ile Tyr Glu
                405                 410                 415

Thr Asn Cys His Trp Ala Asp Cys Thr Lys Glu Tyr Asp Thr Gln Glu
            420                 425                 430

Gln Leu Val His His Ile Asn Asn Glu His Ile His Gly Glu Lys Lys
        435                 440                 445

Glu Phe Val Cys Arg Trp Gln Ala Cys Thr Arg Glu Gln Lys Pro Phe
    450                 455                 460

Lys Ala Gln Tyr Met Leu Val Val His Met Arg Arg His Thr Gly Glu
465                 470                 475                 480

Lys Pro His Lys Cys Thr Phe Glu Gly Cys Ser Lys Ala Tyr Ser Arg
                485                 490                 495

Leu Glu Asn Leu Lys Thr His Leu Arg Ser His Thr Gly Glu Lys Pro
            500                 505                 510

Tyr Val Cys Glu His Glu Gly Cys Asn Lys Ala Phe Ser Asn Ala Ser
        515                 520                 525

Asp Arg Ala Lys His Gln Asn Arg Thr His Ser Asn Glu Lys Pro Tyr
    530                 535                 540

Ile Cys Lys Ile Pro Gly Cys Thr Lys Arg Tyr Thr Asp Pro Ser Ser
545                 550                 555                 560

Leu Arg Lys His Val Lys Thr Val His Gly Pro Asp Ala His Val Thr
                565                 570                 575

Lys Lys Gln Arg Asn Asp Val His Val Arg Ala Pro Leu Leu Lys Glu
            580                 585                 590

Asn Gly Asp Asn Glu Ala Ser Ala Glu Pro Gly Gly Arg Gly Pro Glu
        595                 600                 605
```

```
Glu Ser Val Glu Ala Ser Ser Thr Ser His Thr Val Glu Asp Cys Leu
    610                 615                 620

His Ile Lys Ala Ile Lys Thr Glu Ser Ser Gly Leu Cys Gln Ser Ser
625                 630                 635                 640

Pro Gly Ala Gln Ser Ser Cys Ser Ser Glu Pro Ser Pro Leu Gly Ser
                645                 650                 655

Ala Pro Asn Asn Asp Ala Gly Met Glu Met Pro Gly Thr Gly Pro Gly
            660                 665                 670

Ser Leu Gly Asp Leu Thr Ala Leu Ala Asp Thr Cys Pro Gly Ala Asp
        675                 680                 685

Thr Ser Ala Leu Ala Ala Pro Ser Thr Gly Gly Leu Gln Leu Arg Lys
    690                 695                 700

His Met Ser Thr Val His Arg Phe Glu Gln Leu Lys Arg Glu Lys Leu
705                 710                 715                 720

Lys Ser Leu Lys Asp Ser Cys Ser Trp Ala Gly Pro Ala Pro His Thr
                725                 730                 735

Arg Asn Thr Lys Leu Pro Pro Leu Pro Val Asn Gly Ser Val Leu Glu
            740                 745                 750

Asn Phe Asn Asn Thr Gly Gly Gly Pro Ala Gly Leu Leu Pro Ser
        755                 760                 765

Gln Arg Leu Pro Glu Leu Thr Glu Val Thr Met Leu Ser Gln Leu Gln
    770                 775                 780

Glu Arg Arg Asp Ser Ser Thr Ser Thr Met Ser Ser Ala Tyr Thr Val
785                 790                 795                 800

Ser Arg Arg Ser Ser Gly Ile Ser Pro Tyr Phe Ser Arg Arg Ser
                805                 810                 815

Ser Glu Ala Ser Pro Leu Gly Gly Leu Arg Pro His Asn Ala Ser Ser
            820                 825                 830

Ala Asp Ser Tyr Asp Pro Ile Ser Thr Asp Ala Ser Arg Arg Ser Ser
        835                 840                 845

Glu Ala Ser Gln Cys Ser Gly Gly Pro Gly Leu Leu Asn Leu Thr
    850                 855                 860

Pro Ala Gln Gln Tyr Asn Leu Arg Ala Lys Tyr Ala Ala Ala Thr Gly
865                 870                 875                 880

Gly Pro Pro Pro Thr Pro Leu Pro Gly Leu Asp Arg Val Ser Leu Arg
                885                 890                 895

Thr Arg Leu Ala Leu Leu Asp Ala Pro Glu Arg Ala Leu Pro Gly Ala
            900                 905                 910

Cys Pro His Pro Leu Gly Pro Arg Arg Gly Ser Asp Gly Pro Thr Tyr
        915                 920                 925

Ser His Gly His Gly His Gly Tyr Ala Gly Ala Ala Pro Ala Phe Pro
    930                 935                 940

His Glu Gly Pro Asn Ser Ser Thr Arg Arg Ala Ser Asp Pro Val Arg
945                 950                 955                 960

Arg Pro Asp Pro Leu Ile Leu Pro Arg Val Gln Arg Phe His Ser Thr
                965                 970                 975

His Asn Met Asn Pro Gly Ser Leu Pro Pro Cys Ala Asp Arg Arg Gly
            980                 985                 990

Leu His Val Gln Ser His Pro Ser Val Asp Ser Asn Leu Thr Arg Asn
        995                 1000                1005

Ala Tyr Ser Pro Arg Pro Pro Ser Ile Asn Glu Asn Val Val Met
    1010                1015                1020

Glu Ala Val Ala Ala Gly Val Asp Gly Pro Gly Leu Glu Cys Asp
```

-continued

```
             1025                1030                1035
Leu Gly Leu Val Glu Asp Glu Leu Val Leu Pro Asp Asp Val Val
        1040                1045                1050
Gln Tyr Ile Lys Ala His Thr Gly Gly Thr Leu Asp Asp Gly Ile
        1055                1060                1065
Arg Gln Gly Tyr Pro Thr Glu Gly Thr Gly Phe Pro Glu Asn Ser
        1070                1075                1080
Lys Leu Pro Ser Pro Gly Leu Gln Gly His Arg Arg Leu Ala Ala
        1085                1090                1095
Ala Asp Ser Asn Met Gly Pro Ser Ala Pro Gly Leu Gly Gly Cys
        1100                1105                1110
Gln Leu Ser Tyr Ser Pro Ser Ser Asn Leu Asn Lys Ser Asn Met
        1115                1120                1125
Pro Val Gln Trp Asn Glu Val Ser Ser Gly Thr Val Asp Ala Leu
        1130                1135                1140
Pro Thr Gln Val Lys Pro Pro Phe Pro His Ser Asn Leu Ala
        1145                1150                1155
Val Val Gln Gln Lys Pro Ala Phe Gly Gln Tyr Pro Gly Tyr Asn
        1160                1165                1170
Pro Gln Ser Val Gln Ser Ser Gly Gly Leu Asp Ser Thr Gln
        1175                1180                1185
Pro His Leu Gln Leu Arg Gly Ala Pro Ser Ala Ser Arg Gly Ser
        1190                1195                1200
Tyr Thr Gln Gln Pro Arg Gln Pro Ala Ala Gly Ser Gln Cys Leu
        1205                1210                1215
Gly Met Ser Ala Ala Met Ser Pro Gln Ala Ser Tyr Ser Gln Ala
        1220                1225                1230
His Pro Gln Leu Ser Pro Asn Ile Val Ser Gly Ser Leu Asn Gln
        1235                1240                1245
Phe Ser Pro Ser Cys Ser Asn Met Ala Ala Lys Pro Ser His Leu
        1250                1255                1260
Gly Leu Pro Gln Gln Met Glu Val Val Pro Asn Ala Thr Ile Met
        1265                1270                1275
Asn Gly His Gln Arg Glu His Gly Val Pro Asn Ser Ser Leu Ala
        1280                1285                1290
Ala Val Ser Gln Pro His Pro Val Leu Ser Tyr Pro Gln Gln Asp
        1295                1300                1305
Ser Tyr Gln Gln Gly Ser Asn Leu Leu Ser Ser His Gln Pro Gly
        1310                1315                1320
Phe Met Glu Ser Gln Gln Asn Ala Gly Phe Gly Leu Met Gln Pro
        1325                1330                1335
Arg Pro Pro Leu Glu Pro Asn Thr Ala Ser Arg His Arg Gly Val
        1340                1345                1350
Arg Ser Gly Gln Gln Gln Leu Tyr Ala Arg Thr Thr Gly Gln Ala
        1355                1360                1365
Met Val Thr Ser Ala Asn Gln Glu Thr Ala Glu Ala Met Pro Lys
        1370                1375                1380
Gly Pro Ala Gly Thr Met Val Ser Leu Ala Pro Gln Pro Ser Gln
        1385                1390                1395
Asp Thr Gly Arg Ala Gln Asp Gln Asn Thr Leu Tyr Tyr Tyr Gly
        1400                1405                1410
Gln Ile His Met Tyr Glu Gln Asn Gly Gly Cys Pro Ala Val Gln
        1415                1420                1425
```

```
Pro Gln Pro Pro Gln Pro Gln Ala Cys Ser Asp Ser Ile Gln Pro
    1430            1435                1440
Glu Pro Leu Pro Ser Pro Gly Val Asn Gln Val Ser Ser Thr Val
    1445            1450                1455
Asp Ser Gln Leu Leu Glu Pro Pro Gln Ile Asp Phe Asp Ala Ile
    1460            1465                1470
Met Asp Asp Gly Asp His Ser Leu Phe Ser Gly Ala Leu Ser
    1475            1480                1485
Pro Thr Leu Leu His Asn Leu Ser Gln Asn Ser Ser Arg Leu Thr
    1490            1495                1500
Thr Pro Arg Asn Ser Leu Thr Leu Pro Ser Ile Pro Ala Gly Ile
    1505            1510                1515
Ser Asn Met Ala Val Gly Asp Met Ser Ser Met Leu Thr Ser Leu
    1520            1525                1530
Ala Glu Glu Ser Lys Phe Leu Asn Met Met Thr
    1535            1540

<210> SEQ ID NO 7
<211> LENGTH: 25
<212> TYPE: PRT
<213> ORGANISM: Artificial Sequence
<220> FEATURE:
<223> OTHER INFORMATION: partial sequence

<400> SEQUENCE: 7

Leu Gly Ser Ala Pro Asn Asn Asp Ser Gly Val Glu Met Pro Gly Thr
1               5                   10                  15

Gly Pro Gly Ser Leu Gly Asp Leu Thr
            20                  25

<210> SEQ ID NO 8
<211> LENGTH: 25
<212> TYPE: PRT
<213> ORGANISM: Artificial Sequence
<220> FEATURE:
<223> OTHER INFORMATION: partial sequence

<400> SEQUENCE: 8

Leu Gly Ser Ala Pro Asn Asn Asp Ser Gly Val Glu Met Pro Gly Thr
1               5                   10                  15

Gly Pro Gly Ser Leu Gly Asp Leu Thr
            20                  25

<210> SEQ ID NO 9
<211> LENGTH: 25
<212> TYPE: PRT
<213> ORGANISM: Artificial Sequence
<220> FEATURE:
<223> OTHER INFORMATION: partial sequence

<400> SEQUENCE: 9

Leu Gly Ser Val Pro Asn Asn Asp Ser Gly Val Glu Met Pro Gly Thr
1               5                   10                  15

Gly Pro Gly Ser Leu Gly Asp Leu Thr
            20                  25

<210> SEQ ID NO 10
<211> LENGTH: 25
<212> TYPE: PRT
<213> ORGANISM: Artificial Sequence
<220> FEATURE:
<223> OTHER INFORMATION: partial sequence
```

```
<400> SEQUENCE: 10

Leu Gly Ser Ala Pro Asn Asn Asp Ser Gly Val Glu Met Pro Gly Thr
1               5                   10                  15

Gly Pro Gly Ser Leu Gly Asp Leu Thr
            20                  25

<210> SEQ ID NO 11
<211> LENGTH: 25
<212> TYPE: PRT
<213> ORGANISM: Artificial Sequence
<220> FEATURE:
<223> OTHER INFORMATION: partial sequence

<400> SEQUENCE: 11

Leu Gly Ser Ala Thr Asn Asn Asp Ser Gly Val Glu Met Ala Met His
1               5                   10                  15

Ser Gly Gly Ser Leu Gly Asp Leu Ser
            20                  25

<210> SEQ ID NO 12
<211> LENGTH: 26
<212> TYPE: PRT
<213> ORGANISM: Artificial Sequence
<220> FEATURE:
<223> OTHER INFORMATION: partial seqeunce

<400> SEQUENCE: 12

Pro Ser Pro Tyr Ser Asn Tyr Ile Asp Ser Gly Val Asp Val Ser Leu
1               5                   10                  15

His Gly Glu Gly Ser Leu Gly Asp Leu Leu
            20                  25

<210> SEQ ID NO 13
<211> LENGTH: 26
<212> TYPE: PRT
<213> ORGANISM: Artificial Sequence
<220> FEATURE:
<223> OTHER INFORMATION: partial sequence

<400> SEQUENCE: 13

Pro Leu Gly Ser Thr Asn Asn Asn Asp Ser Gly Val Glu Met Asn Met
1               5                   10                  15

His Gly Gly Gly Ser Leu Gly Asp Leu Thr
            20                  25
```